United States Patent
Suto et al.

(10) Patent No.: US 11,447,472 B2
(45) Date of Patent: Sep. 20, 2022

(54) POLYMOROPHS OF 5-AZA-4'-THIO-2'-DEOXYCYTIDINE

(71) Applicants: Southern Research Institute, Birmingham, AL (US); PINOTBIO, INC., Gyeonggi-do (KR)

(72) Inventors: Mark J. Suto, Homewood, AL (US); Doo Young Jung, Daejeon (KR); Jin Soo Lee, Gyeonggi-do (KR); Hyunyong Cho, Gyeonggi-do (KR)

(73) Assignees: PINOTBIO, INC., Suwon-si (KR); SOUTHERN RESEARCH INSTITUTE, Birmingham, AL (US)

( * ) Notice: Subject to any disclaimer, the term of this patent is extended or adjusted under 35 U.S.C. 154(b) by 0 days.

(21) Appl. No.: 17/384,345

(22) Filed: Jul. 23, 2021

(65) Prior Publication Data

US 2022/0024903 A1 Jan. 27, 2022

Related U.S. Application Data

(60) Provisional application No. 63/055,754, filed on Jul. 23, 2020.

(51) Int. Cl.
*C07D 409/04* (2006.01)
*A61P 35/00* (2006.01)

(52) U.S. Cl.
CPC ............ *C07D 409/04* (2013.01); *A61P 35/00* (2018.01); *C07B 2200/13* (2013.01)

(58) Field of Classification Search
CPC .... C07D 409/04; A61P 35/00; C07B 2200/13
USPC ....................................................... 514/241
See application file for complete search history.

(56) References Cited

U.S. PATENT DOCUMENTS

| 5,591,722 | A | 1/1997 | Montgomery et al. |
| 6,020,322 | A | 2/2000 | von Borstel et al. |
| 8,846,628 | B2 | 9/2014 | Etter et al. |
| 2006/0014949 | A1 | 1/2006 | Redkar et al. |
| 2011/0218170 | A1 | 9/2011 | Thottassery et al. |
| 2016/0312261 | A1 | 10/2016 | Pascual Gilabert et al. |
| 2018/0008608 | A1 | 9/2018 | Paolo et al. |
| 2019/0240210 | A1 | 8/2019 | Seki et al. |

FOREIGN PATENT DOCUMENTS

| AU | 2019256465 | 4/2019 |
| CA | 3097003 | 4/2019 |
| CN | 2019800371089 | 4/2019 |
| EP | 19789422.3 | 4/2019 |
| JP | 2020-557913 | 4/2019 |
| KR | 20110015629 | 2/2011 |
| KR | 10-2020-7033020 | 4/2019 |
| WO | WO2011/109012 A1 | 9/2011 |
| WO | PCT/US2019/028168 | 4/2019 |
| WO | WO 2019/204637 | 10/2019 |
| WO | PCT/US2021/028726 | 4/2021 |
| WO | PCT/US2021/043021 | 7/2021 |

OTHER PUBLICATIONS

Musther et al. (2014) "Animal Versus Human Oral Drug Bioavailability: Do they Correlate," European Journal of Pharmaceutical Sciences 57: 280-291.
Pubchem CID 49866753, created on Feb. 17, 2011.
Secrist et al. (1991) "Synthesis and biological activity of 2'-deoxy-4'-thio pyrimidine nucleosides" Journal of Med. Chem. 34(8): 2361-6.
Thottassery, et al. (2014) "Novel DNA methyltransferase-1 (DNMT1) depleting anticancer nucleosides, 4'-thio-2'-deoxycytidine and 5-aza-4'-thio-2'-deoxycytidine" Cancer Chemother Pharmacol 74(2): 291-302.
Uenishi et al. (1994) "Syntheses and antitumor activities of D- and L-2'-deoxy-4'-thio pyrimidine nucleosides" Nucleosides & Nucleotides 13(6-7): 1347-61.
Wishka et al. (2021) "The development of β-selective glycosylation reactions with benzyl substituted 2-deoxy-1,4-dithio-D-erythro-pentafuranosides: enabling practical multi-gram synthesis of 4'-Thio-2'-deoxycytidine (T-dCyd) and 5-aza-4'-thio-2'-deoxycytidine (aza-T-dCyd) to support clinical development," Nucleosides, Nucleotides & Nucleic Acids 40(1), Oct. 16, 2020.
Written Opinion of the International Searching Authority for PCT/US21/43021 dated Dec. 15, 2021.
International Search Report for PCT/US21/43021 dated Dec. 15, 2021.
U.S. Appl. No. 62/660,208, filed Apr. 19, 2018, Moukha-Chafiq et al.
U.S. Appl. No. 17/045,986, filed Oct. 7, 2020, Moukha-Chafiq et al.
U.S. Appl. No. 63/014,346, filed Apr. 23, 2020, Lee et al.
U.S. Appl. No. 17/238,182, filed Apr. 22, 2021, Suto, et al.
U.S. Appl. No. 63/055,754, filed Jul. 23, 2020, Suto et al.

*Primary Examiner* — Yevgeny Valenrod
(74) *Attorney, Agent, or Firm* — Sughrue Mion, PLLC

(57) ABSTRACT

The present disclosure provides crystalline polymorphs of 5-aza-4'-thio-2'-deoxycytidine. The crystalline polymorphs may be formulated in a pharmaceutical composition, optionally in combination with an additional chemotherapeutic agent. The crystalline polymorphs are useful to treat various diseases including blood cancers, such as myelodysplastic syndrome and leukemia. A process for preparing the crystalline polymorphs of 5-aza-4'-thio-2'-deoxycytidine is also disclosed. This abstract is intended as a scanning tool for purposes of searching in the particular art and is not intended to be limiting of the present invention.

22 Claims, 29 Drawing Sheets

POLYMOROPHS OF 5-AZA-4'-THIO-2'-DEOXYCYTIDINE

CROSS-REFERENCE TO RELATED APPLICATIONS

This Application claims the benefit of U.S. Application No. 63/055,754, filed on Jul. 23, 2020, the contents of which are hereby incorporated by reference in their entirety.

BACKGROUND

Decitabine (also known as Dacogen® or 5-aza-2'-deoxycytidine) is a pyrimidine nucleoside analog of cytidine that induces DNA hypomethylation by inhibiting DNA methyltransferase. Specifically, decitabine functions by incorporating into DNA strands upon replication, and then, when DNA methyltransferases (DNMTs) such as DNMT1 are engaged to bind the DNA and to replicate the methylation to the daughter strand, DNMTs are bound to decitabine irreversibly and cannot disengage. As such, decitabine action is division-dependent; the cells have to divide in order for the pharmaceutical to act. Therefore, cells that divide much more rapidly than most other cells in the body (e.g., cancer cells) will be more severely affected by decitabine. It is used for the treatment of cancers such as myelodysplastic syndromes (MDS) and leukemia, including acute myeloid leukemia (AML), in which DNA hypermethylation is critical for their development.

5-Aza-4'-thio-2'-deoxycytidine ("aza-T-dCyd") is a thio-substituted derivative of decitabine that was subjected to early clinical evaluation by the National Cancer Institute (NCI). This DNMT1 inhibitor has recently attracted attention due to high DNMT removal and inhibitory activities in cells, a reduced rate of degradation by cytidine deaminase, and a relatively low generation of toxic by-products compared to conventional compounds with a 5-azacytidine backbone. Like decitabine, aza-T-dCyd can be prepared in various forms and crystalline structures.

U.S. Pat. No. 5,591,722 relates to 2'-deoxy-4'-thioribonucleosides and intermediates useful to treat viral diseases and describes a generic formula covering 5-azacytidine compounds. U.S. Patent Publication No. 2006/0014949 reports polymorphs of decitabine. Thottassery, et al. (*Cancer Chemother Pharmacol,* 2014) reports aza-T-dCyd. Clinical trial NCT04167917 reports a Phase I trial of Aza-T-dCyd in MDS and AML with an anticipated completion of 2025. Despite these advances, polymorphs of aza-T-dCyd have thus far remained elusive.

SUMMARY

In accordance with the purpose(s) of the invention, as embodied and broadly described herein, the invention, in an embodiment, relates to crystalline polymorphs of aza-T-dCyd, which can be useful in, for example, treating cancers such as, for example, MDS and leukemia.

Thus, disclosed are crystalline polymorphs of 5-aza-4'-thio-2'-deoxycytidine, wherein the crystalline polymorph has a powder X-ray diffraction pattern that contains peaks at about 8°, about 13°, about 15°, about 17°, about 19°, about 22°, about 230 about 26°, about 28°, about 29°, about 31°, about 33°, and about 37° 2θ.

Also disclosed are crystalline polymorphs of 5-aza-4'-thio-2'-deoxycytidine, wherein the crystalline polymorph has a powder X-ray diffraction pattern that contains peaks at about 6°, about 12°, about 13°, about 14°, about 16°, about 18°, about 20°, about 21°, about 22°, about 26°, about 27°, about 29°, about 30°, about 33°, about 35°, about 36°, about 39°, and about 41° 2θ.

Also disclosed is an aza-T-dCyd compound consisting of a crystalline polymorph which has a powder X-ray diffraction pattern that contains peaks at about 8°, about 12°, about 13°, about 17°, about 19°, about 22°, about 23° about 26°, about 28°, about 29°, about 31°, about 33°, and about 37° 2θ.

Also disclosed is an aza-T-dCyd compound consisting of a crystalline polymorph which has a powder X-ray diffraction pattern that contains peaks at about 6°, about 12°, about 13°, about 14°, about 16°, about 18°, about 20°, about 21°, about 22°, about 26°, about 27°, about 29°, about 30°, about 33°, about 35°, about 36°, about 39°, and about 41° 2θ.

Also disclosed are crystalline polymorphs of aza-T-dCyd, wherein the crystalline polymorph is Form A or Form F.

Also disclosed are pharmaceutical compositions comprising a therapeutically effective amount of a disclosed crystalline polymorph, and a pharmaceutically acceptable carrier.

Also disclosed are methods of treating cancer in a subject in need thereof, the method comprising administering to the subject an effective amount of a disclosed crystalline polymorph, thereby treating cancer in the subject. Examples of cancer include, but are not limited to, myelodysplastic syndrome and leukemia.

Also disclosed are methods of making a disclosed crystalline polymorph or a disclosed composition.

Also disclosed are methods of making a disclosed crystalline polymorph, the method comprising subjecting aza-T-dCyd to one or more of solvent equilibration, evaporative crystallization, anti-solvent addition, thermocycling crystallizaiton, sonication, and vapor diffusion into solution.

Also disclosed are kits comprising a disclosed crystalline polymorph, and one or more of: (a) at least one chemotherapeutic agent; (b) instructions for administering the composition in connection with treating cancer; and (c) instructions for treating cancer.

While embodiments of the present invention can be described and claimed in a particular statutory class, such as the system statutory class, this is for convenience only and one of skill in the art will understand that each embodiment of the present invention can be described and claimed in any statutory class. Unless otherwise expressly stated, it is in no way intended that any method or embodiment set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of embodiments described in the specification.

BRIEF DESCRIPTION OF THE DRAWINGS

The drawings described herein are for illustrative purposes only of selected embodiments and not all possible implementations, and are not intended to limit the scope of the present disclosure.

FIG. 7A shows a representative LC chromatogram of aza-T-dCyd starting material (SM). FIG. 7B shows a representative MS spectrum of aza-T-dCyd from the liquid chromatography.

FIG. 8A shows the LC chromatogram of aza-T-dCyd formulated in water. FIG. 8B shows the MS spectrum of an impurity eluted at 3.8 minutes. FIG. 8C shows the MS spectrum of aza-T-dCyd eluted at 4.4 minutes.

FIG. 13A shows the TGMS analysis of Form A. FIG. 13B shows the DSC analysis of Form A. FIG. 13C shows the LCMS analysis of Form A.

FIG. 15A shows the TGMS analysis of Form F. FIG. 15B shows the DSC analysis of Form F. FIG. 15C shows the LCMS analysis of Form F.

Figure 1:
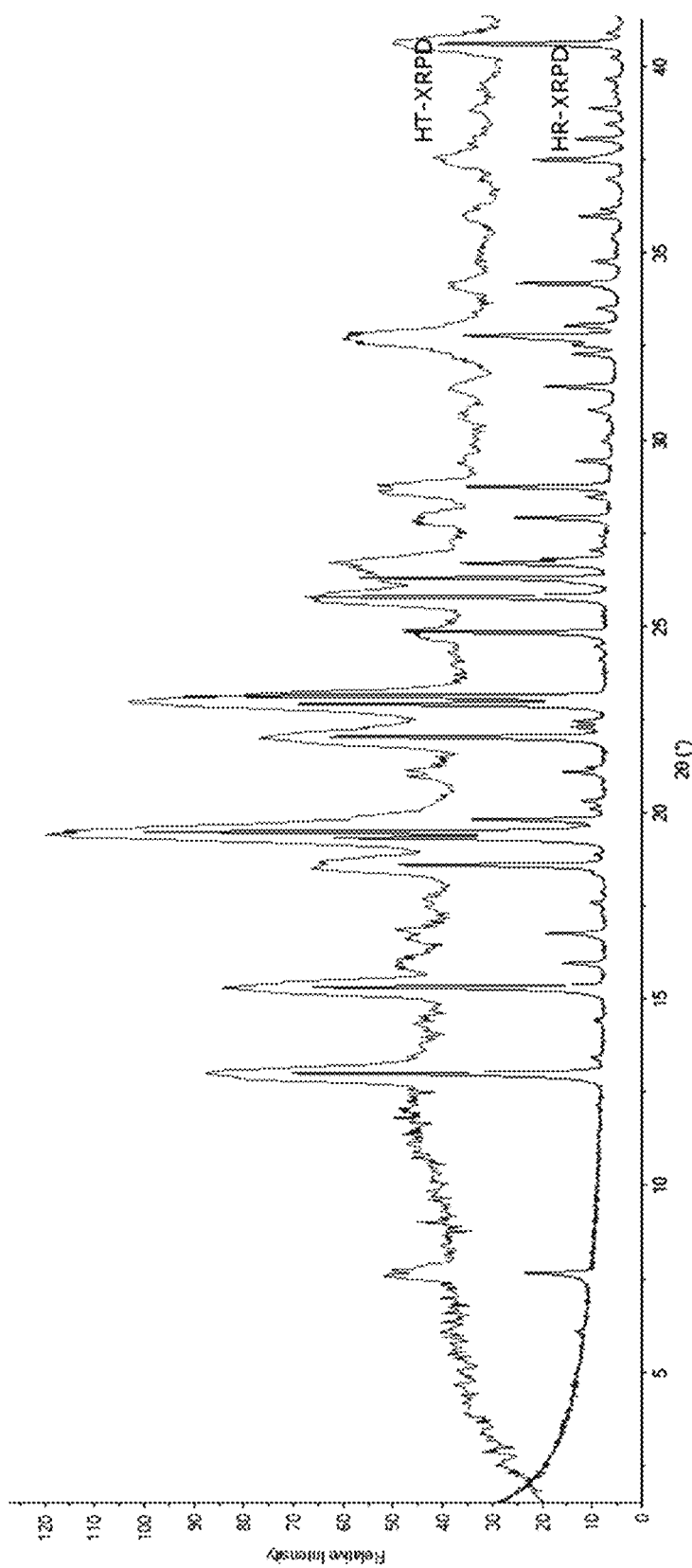
FIG. 1 shows representative HT-XRPD and HR-XRPD patterns for aza-T-dCyd starting material (SM: aza-T-dCyd that has not yet been subjected to specific crystallization conditions).

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein. The following description is merely exemplary in nature and is not intended to limit the present disclosure, application, or uses.

While embodiments of the present invention can be described and claimed in a particular statutory class, such as the system statutory class, this is for convenience only and one of skill in the art will understand that each embodiment of the present invention can be described and claimed in any statutory class. Unless otherwise expressly stated, it is in no way intended that any method or embodiment set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of embodiments described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

As used in the specification and the appended claims, the singular forms "a," "an," and "the" include plural referents unless the context clearly dictates otherwise. Thus, for example, reference to "a functional group," "an alkyl," or "a residue" includes mixtures of two or more such functional groups, alkyls, or residues, and the like.

As used in the specification and in the claims, the term "comprising" can include the embodiments "consisting of" and "consisting essentially of."

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself.

For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated+10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, "$EC_{50}$," is intended to refer to the effective concentration of a substance (e.g., a compound or a drug) that is required for 50% inhibition of a biological process, or component of a process, including a protein, subunit, organelle, ribonucleoprotein, etc. In one embodiment, an $EC_{50}$ can refer to the concentration of a substance that is required for 50% inhibition in vivo, as further defined elsewhere herein.

As used herein, the terms "optional" or "optionally" means that the subsequently described event or circumstance can or cannot occur, and that the description includes instances where said event or circumstance occurs and instances where it does not.

5-Aza-4'-thio-2'-deoxycytidine (also known as NTX-301) refers to a modified cytidine nucleoside where the ring oxygen on the sugar moiety of the nucleoside is replaced with a sulfur. Aza-T-dCyd has the following structure:

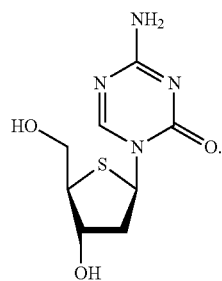

Unless otherwise noted, the term "aza-T-dCyd" includes the compound itself and also pharmaceutically acceptable salts thereof.

Crystalline polymorphs of aza-T-dCyd refer to various crystal structures of the nucleoside. In some embodiments, the crystalline polymorph of aza-T-dCyd refers to Form A, Form B, Form C1, Form C2, Form D1, Form D2, Form E, Form F, Form G1, Form G2, Form H, Form 1, or Form J as further described in the present specification including Examples. In particular embodiments, the crystalline polymorph is Form A or Form F.

The term "substantially similar to," as used herein, refers to a powder X-ray diffraction pattern that is non-identical to those depicted herein but shares a majority of major peaks, which fall within the limits of experimental error. For example, in various aspects, a substantially similar powder X-ray diffraction pattern can share at least 3 peaks, at least 4 peaks, at least 5 peaks, at least 6 peaks, at least 7, at least 8 peaks, at least 9 peaks, at least 10 peaks, or more than 10 peaks with the powder X-ray diffraction patterns disclosed herein.

Figure 11:
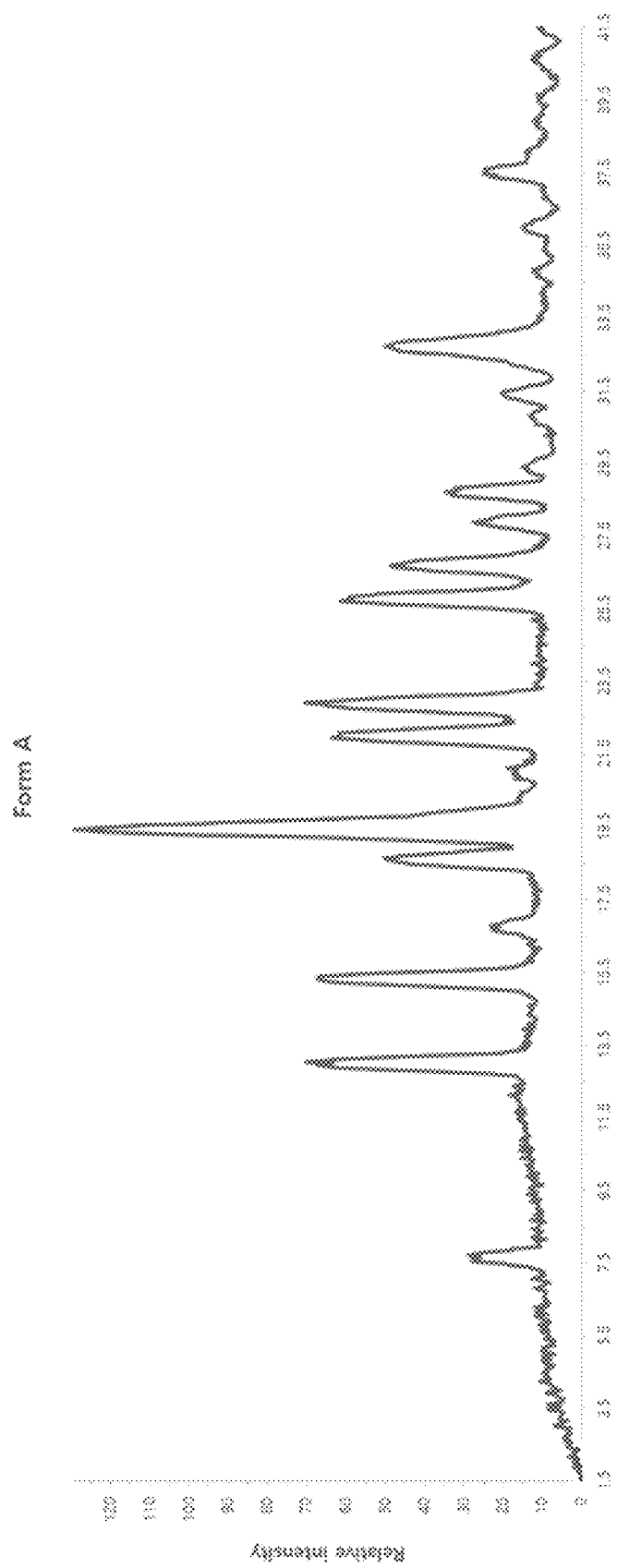
FIG. 11 shows a representative XRPD pattern of Form A of aza-T-dCyd.

The term "polymorph Form A" or "Form A" refers to a crystalline form of aza-T-dCyd that exhibits an X-ray powder diffraction pattern substantially the same as that shown in FIG. 11. In an embodiment, Form A has an XRPD pattern with peaks at about 8°, about 13°, about 15°, about 17°, about 19°, about 22°, about 23° about 26°, about 28°, about 29°, about 310, about 33°, and about 37° 2θ. In another embodiment, Form A has an XRPD pattern with peaks at 7.7°±0.3°, 13.02°±0.3°, 15.34°±0.3°, 16.78°±0.3°, 18.62°±0.3°, 19.42°±0.3°, 21.94°±0.3°, 22.90°±0.3°, 25.70°±0.3°, 26.64°±0.3°, 27.86°±0.3°, 28.63°±0.3°, 29.45°±0.3°, 31.42°±0.3°, 32.70°±0.3°, 34.72°±0.3°, 35.97°±0.3°, and 37.46°±0.3°2θ. In a particular embodiment, Form A has an XRPD pattern with peaks at 7.7°, 13.02°, 15.34°, 16.78°, 18.62°, 19.42°, 21.94°, 22.90°, 25.70°, 27.86°, 28.70°, 31.42°, 32.70°, and 37.46° 2θ.

Figure 12:
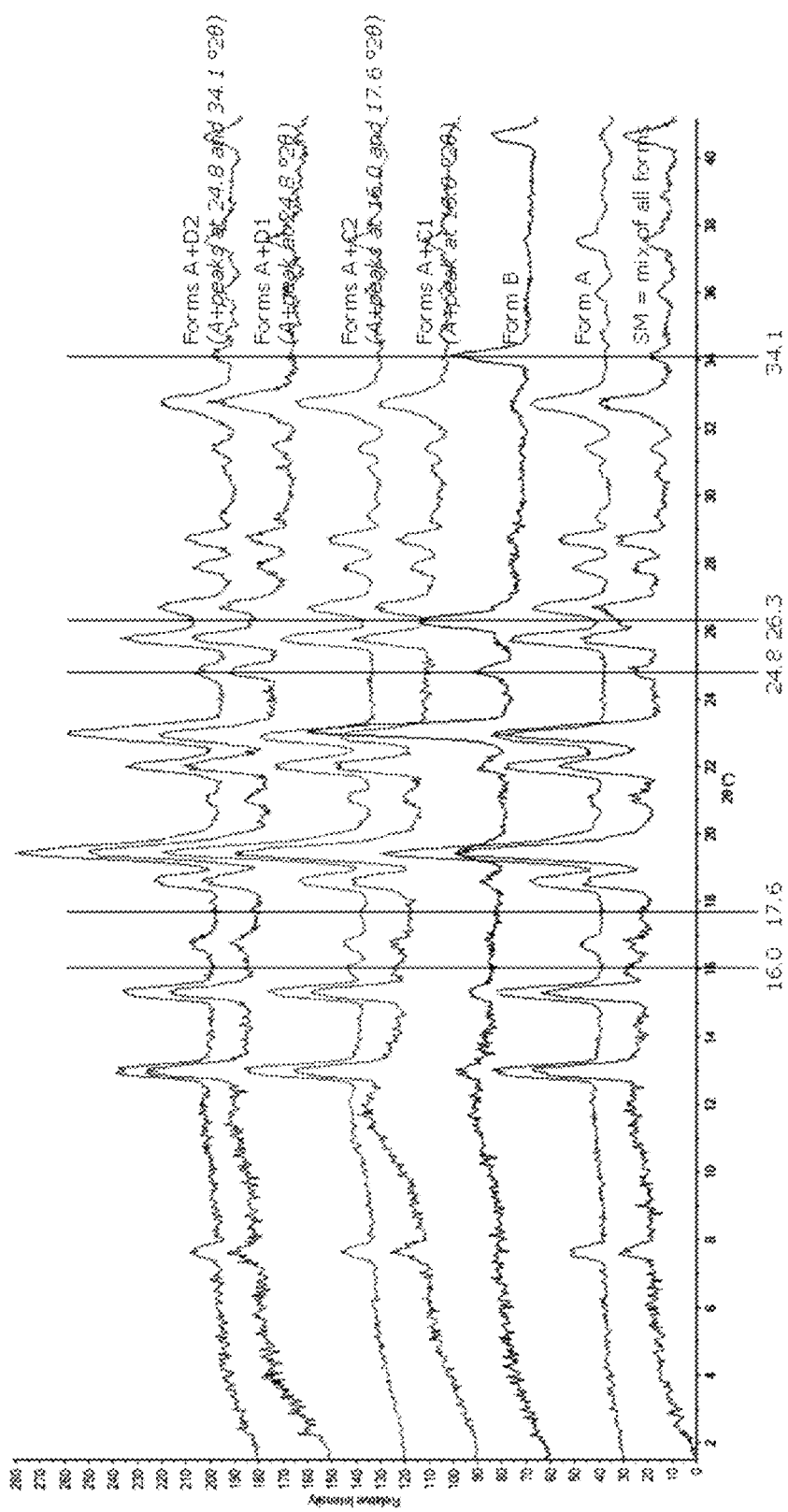
FIG. 12 shows representative XRPD patterns of Forms A, B, A+C1, A+C2, A+D1, and A+D2 of aza-T-dCyd, and aza-T-dCyd starting material (SM).
Figure 13A:
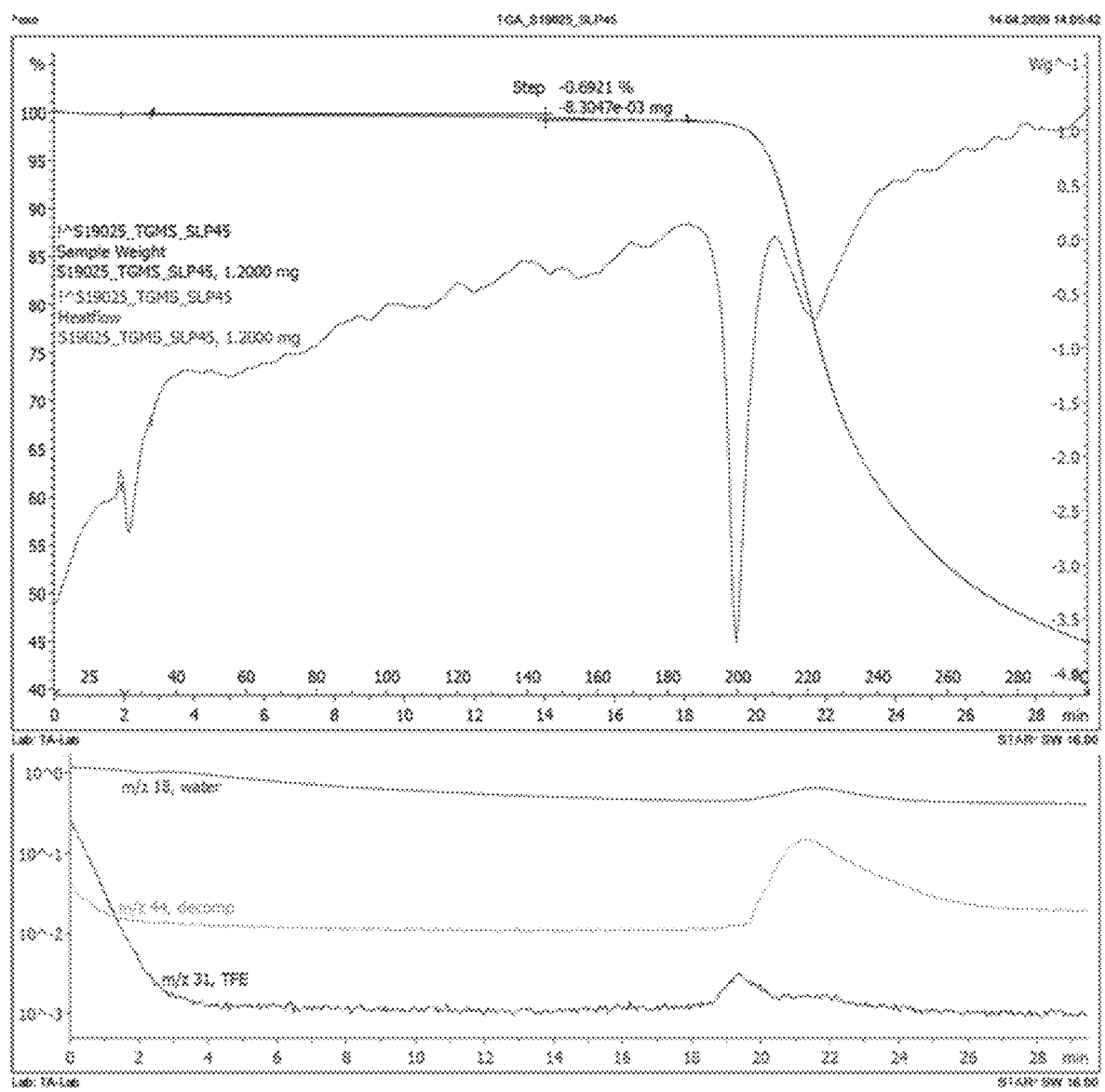
FIG. 13A-C show representative chemical analyses of Form A. Specifically.
Figure 13B:
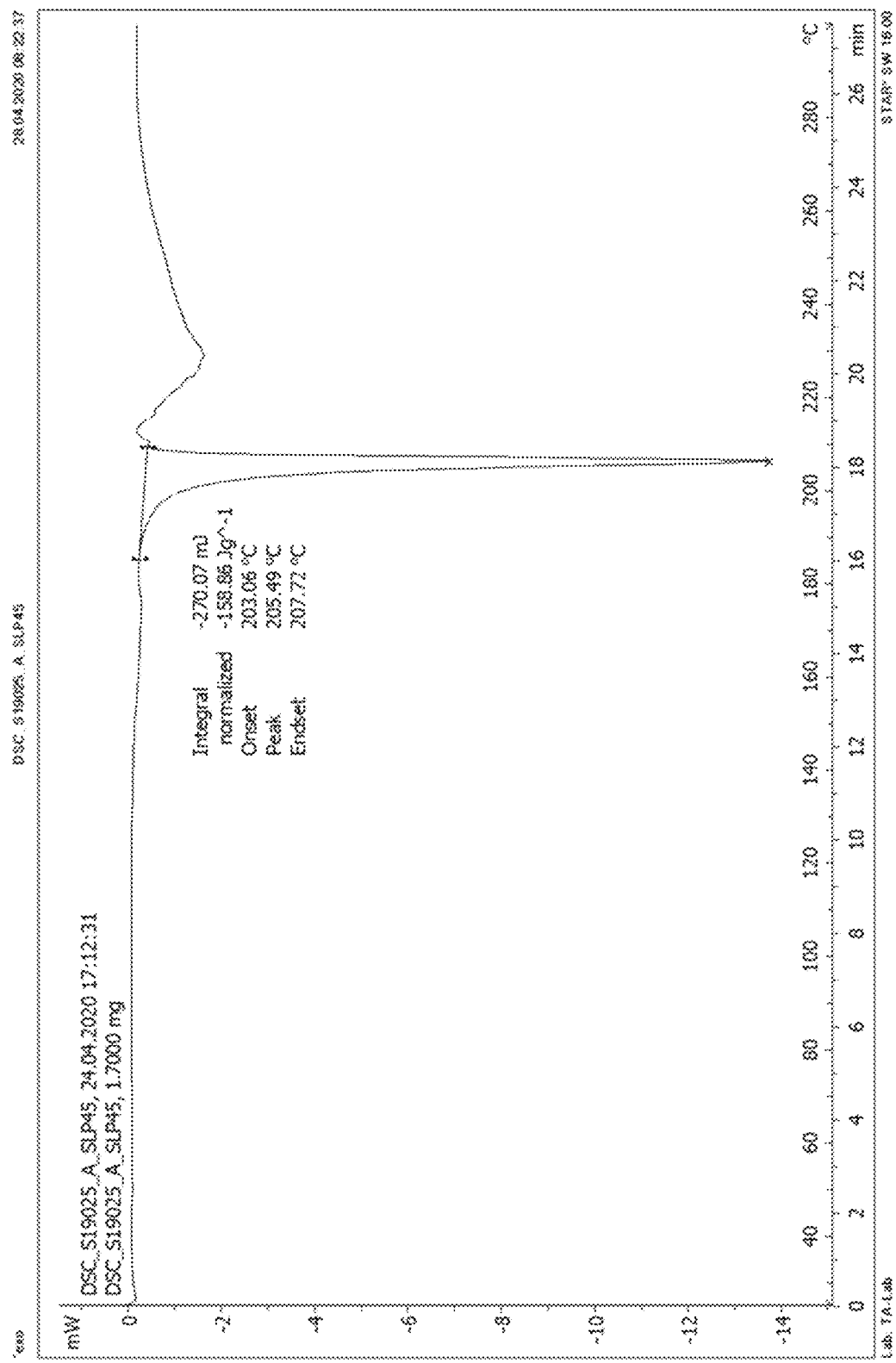
Figure 13C:
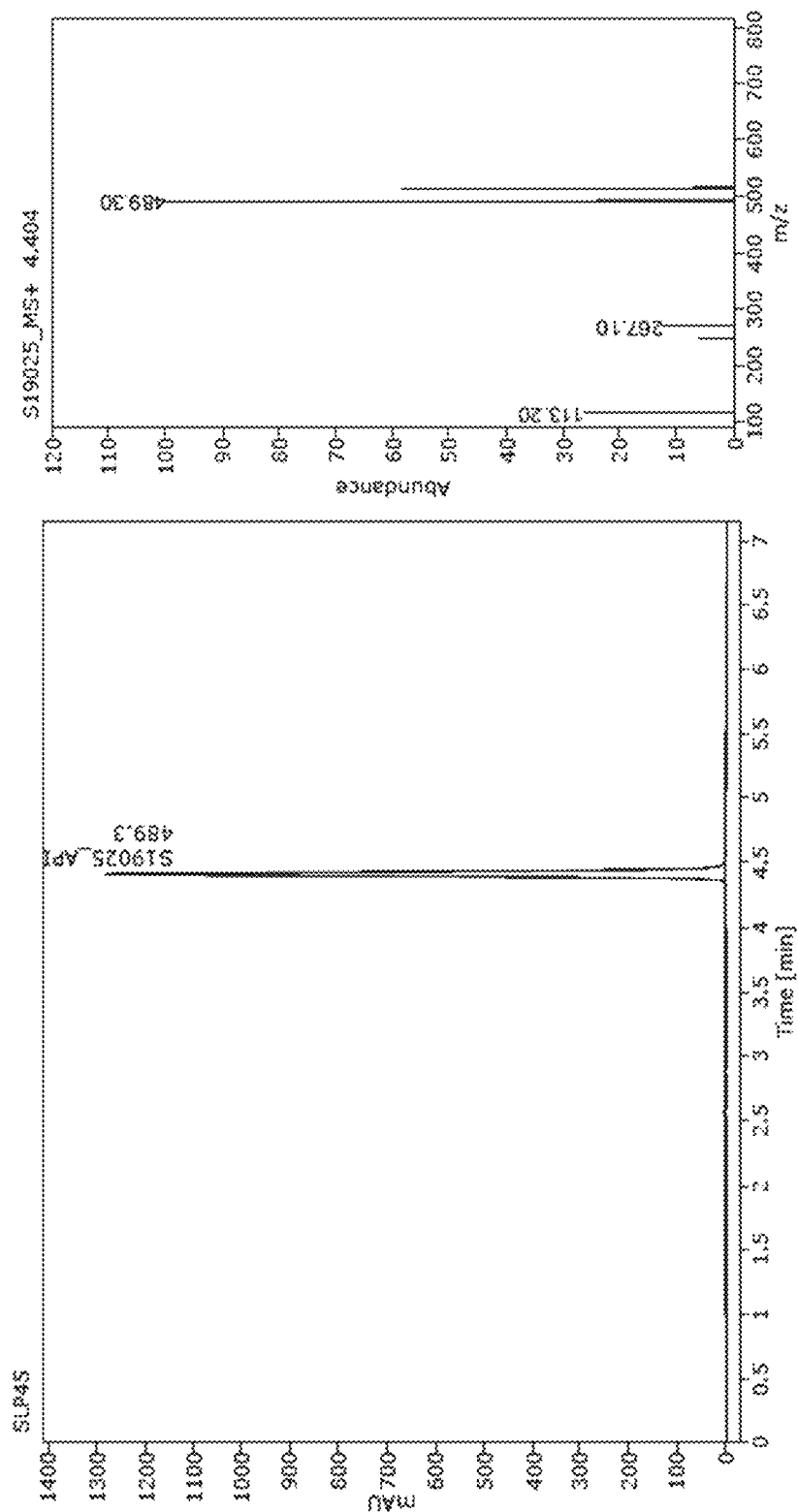

The term "polymorph Form B" or "Form B" refers to a crystalline form of aza-T-dCyd that exhibits an X-ray powder diffraction pattern substantially the same as that shown in FIG. 12.

The term "polymorph Form C1" or "Form C1" refers to a crystalline form of aza-T-dCyd that appears in a mixture with Form A and exhibits an X-ray powder diffraction pattern substantially the same as that shown in FIG. 12.

The term "polymorph Form C2" or "Form C2" refers to a crystalline form of aza-T-dCyd that appears in a mixture with Form A and exhibits an X-ray powder diffraction pattern substantially the same as that shown in FIG. 12.

The term "polymorph Form D1" or "Form D1" refers to a crystalline form of aza-T-dCyd that appears in a mixture with Form A and exhibits an X-ray powder diffraction pattern substantially the same as that shown in FIG. 12.

The term "polymorph Form D2" or "Form D2" refers to a crystalline form of aza-T-dCyd that exhibits an X-ray powder diffraction pattern substantially the same as that shown in FIG. 12.

Figure 14:
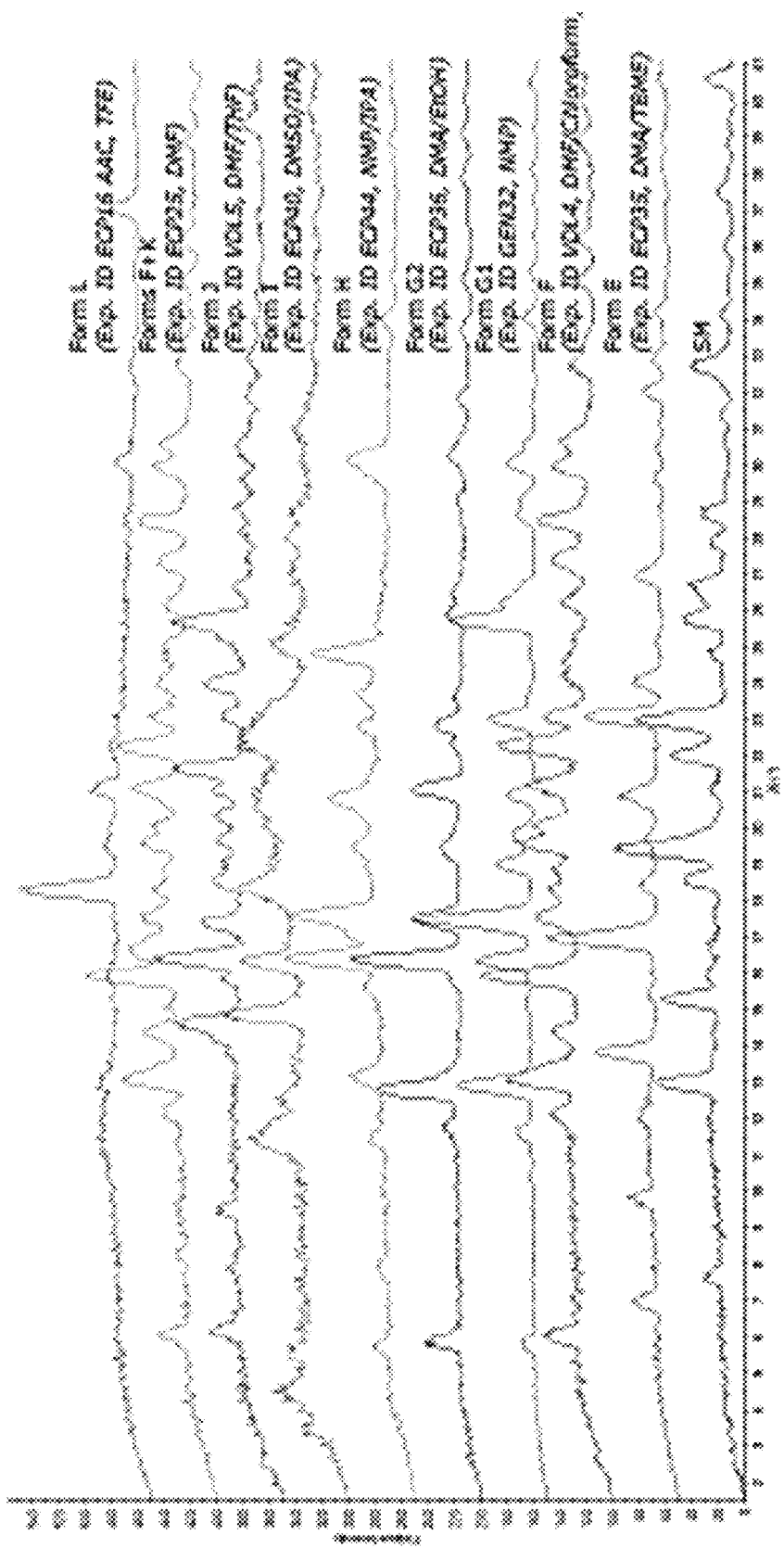
FIG. 14 shows representative XRPD patterns of Forms E, F, G1, G2, H, I, J, F+K, and L of aza-T-dCyd, and aza-T-dCyd starting material (SM).

The term "polymorph Form E" or "Form E" refers to a crystalline form of aza-T-dCyd that exhibits an X-ray powder diffraction pattern substantially the same as that shown in FIG. 14.

Figure 16:
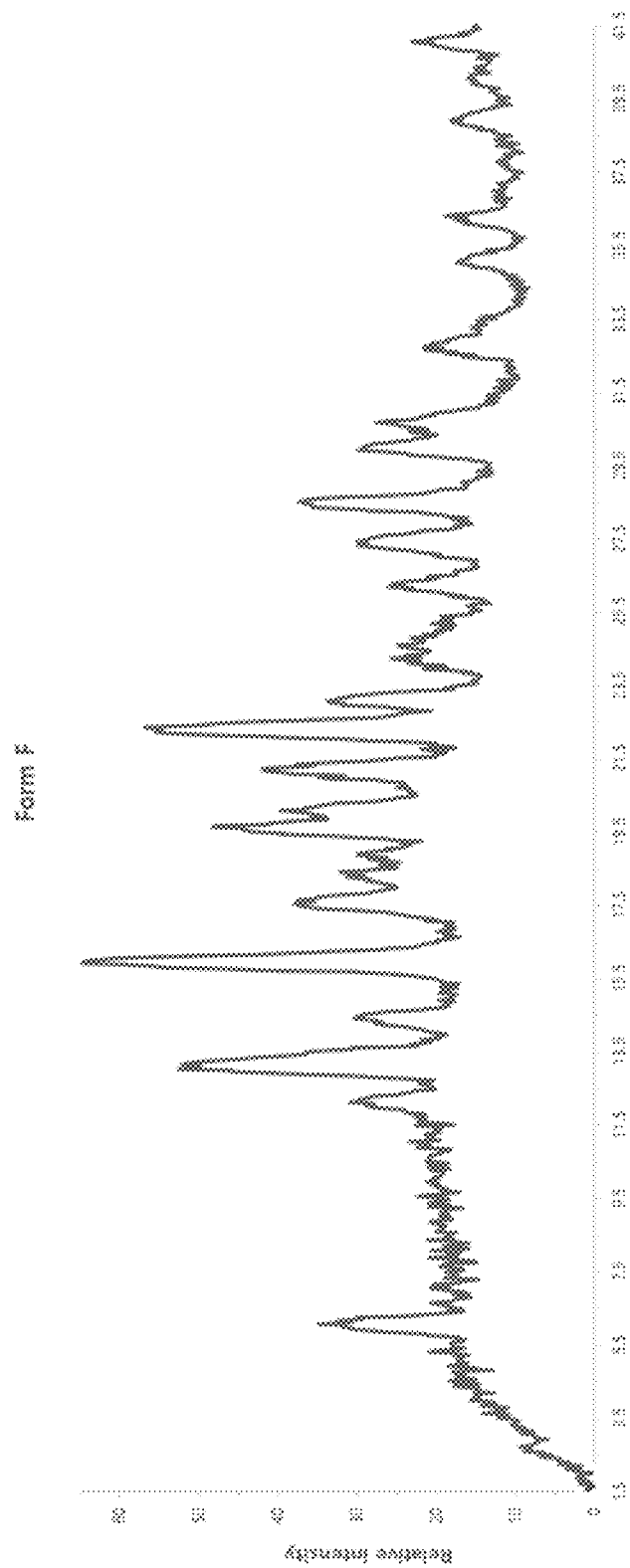
FIG. 16 shows a representative XRPD pattern of Form F of aza-T-dCyd.

The term "polymorph Form F" or "Form F" refers to a crystalline form of aza-T-dCyd that exhibits an X-ray powder diffraction pattern substantially the same as that shown in FIG. 16. In an embodiment, Form F has an XRPD pattern with peaks at about 6°, about 12°, about 13°, about 14°, about 16°, about 18°, about 20°, about 21°, about 22°, about 26°, about 27°, about 29°, about 30°, about 33, about 35°, about 36°, about 39°, and about 41° 2θ. In an embodiment, Form F has an XRPD pattern with peaks at 6.06°±0.3°, 12.10°±0.3°, 13.02°±0.3°, 14.38°±0.3°, 15.94°±0.3°, 17.50°±0.3°, 19.62°±0.3°, 21.18°±0.3°, 22.34°±0.3°, 26.18°±0.3°, 27.42°±0.3°, 28.50°±0.3°, 29.90°±0.3°, 32.66°±0.3°, 35.02°±0.3°, 36.30°±0.3°, 38.94°±0.3°, and 41.06°±0.3° 2θ. In a particular embodiment, Form F has an XRPD pattern with peaks at 6.06°, 12.10°, 13.02°, 14.38°, 15.94°, 17.50°, 19.62°, 21.18°, 22.34°, 26.18°, 27.42°, 28.50°, 29.90°, 32.66°, 35.02°, 36.30°, 38.94°, and 41.06° 2θ.

The term "polymorph Form G1" or "Form G1" refers to a crystalline form of aza-T-dCyd that exhibits an X-ray powder diffraction pattern substantially the same as that shown in FIG. 14.

The term "polymorph Form G2" or "Form G2" refers to a crystalline form of aza-T-dCyd that exhibits an X-ray powder diffraction pattern substantially the same as that shown in FIG. 14.

The term "polymorph Form H" or "Form H" refers to a crystalline form of aza-T-dCyd that exhibits an X-ray powder diffraction pattern substantially the same as that shown in FIG. 14.

The term "polymorph Form I" or "Form I" refers to a crystalline form of aza-T-dCyd that exhibits an X-ray powder diffraction pattern substantially the same as that shown in FIG. 14.

The term "polymorph Form J" or "Form J" refers to a crystalline form of aza-T-dCyd that exhibits an X-ray powder diffraction pattern substantially the same as that shown in FIG. 14.

The term "polymorph Form K" or "Form K" refers to a crystalline form of aza-T-dCyd that exhibits an X-ray powder diffraction pattern substantially the same as that shown in FIG. 14.

The term "polymorph Form L" or "Form L" refers to a crystalline form of aza-T-dCyd that exhibits an X-ray powder diffraction pattern substantially the same as that shown in FIG. 14.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one embodiment, the subject is a mammal. In a further embodiment, the mammal is a human. In one embodiment, the subject suffers from blood cancer. In one embodiment, the subject is an animal that can receive administration of the aza-T-dCyd composition.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various embodiments, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one embodiment, the subject is a mammal such as a primate, and, in a further embodiment, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various embodiments, a preparation can be administered therapeutically; that is, administered to treat an existing disease or condition. In further various embodiments, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, the term "therapeutically effective amount," as used herein, refers to an amount of the crystalline polymorph of aza-T-dCyd sufficient to achieve a therapeutic effect. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In a particular embodiment, the therapeutically effective amount is between about 30 mg/m$^2$ and about 70 mg/m$^2$. In another embodiment, the therapeutically effective amount is between about 35 mg/m$^2$ and about 45 mg/m$^2$, between about 45 mg/m$^2$ and about 55 mg/m$^2$, or between about 55 mg/m$^2$ and about 66 mg/m$^2$. In further various embodiments, a preparation can be administered in a "prophylactically effective amount"; that is, an amount effective for prevention of a disease or condition.

As used herein, "dosage form" means a pharmacologically active material in a medium, carrier, vehicle, or device suitable for administration to a subject. A dosage forms can comprise inventive a disclosed compound, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene 9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed compound, a product of a disclosed method of making, or a salt, solvate, or polymorph thereof, suspended in sterile saline solution for injection together with a preservative.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form, which may be supplied on computer readable memory device or downloaded from an internet website, or as recorded presentation. Instructions can comprise one or multiple documents, and are meant to include future updates.

As used herein, the term "cancer" includes neoplasia and dysplasia. The cancer may be blood cancer or a solid cancer. The term "blood cancer" includes neoplasia and dysplasia of blood cells. In some embodiments, the blood cancer is selected from the group consisting of non-Hodgkin's lymphoma, Hodgkin's lymphoma, multiple myeloma, leukemia, lymphoma, myelodysplastic syndrome, acute lymphocytic leukemia, acute myelogenous leukemia, chronic lymphocytic leukemia, chronic myeloid leukemia, and solitary myeloma. The term "solid cancer" includes neoplasia and dysplasia of a tissue or organ. In some embodiments, the cancer may be one or more of stomach cancer, kidney cancer, ovarian cancer, cervical cancer, uterine cancer, prostate cancer, lung cancer, colon cancer, breast cancer, melanoma, and pancreatic cancer.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14$^{th}$ edition), the Physicians' Desk Reference (64$^{th}$ edition), and The Pharmacological Basis of Therapeutics (12$^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term "therapeutic agent" also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, the term "chemotherapeutic agent" refers to compounds and compositions having anti-cancer properties. In an embodiment, the chemotherapeutic agent is combined with the crystalline polymorph of aza-T-dCyd. In an embodiment, the chemotherapeutic agent is selected from the group consisting of an alkylating agent, an antimetabolite agent, an antineoplastic antibiotic agent, a mitotic inhibitor agent, and an mTOR inhibitor agent. In a particular embodiment, the antineoplastic antibiotic agent is selected from the group consisting of doxorubicin, mitoxantrone, bleomycin, daunorubicin, epirubicin, idarubicin, plicamycin, mitomycin, pentostatin, and valrubicin, or pharmaceutically acceptable salts thereof. In a particular embodiment, the antimetabolite agent is selected from the group consisting of gemcitabine, 5-fluorouracil, capectiabine, hydroxyurea, mercaptopurine, pemetrexed, fludarabine, nelarabine, cladribine, clofarabine, cytarabine, decitabine, pralatrexate, floxuridine, methotrexate, and thioguanine, or pharmaceutically acceptable salts thereof. In a particular embodiment, the alkylating agent is selected from the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or pharmaceutically acceptable salts thereof. In a particular embodiment, the mitotic inhibitor agent is selected from the group consisting of irinotecan, topotecan, rubitecan, cabazitaxel docetaxel, paclitaxel, etopside, vincristine, exabepilone, vinorelbine, vinblastine, and teniposide, or pharmaceutically acceptable salts thereof. In a particular embodiment, the mTOR inhibitor agent is selected from the group consisting of everolimus, sirolimus, and temsirolimus, or pharmaceutically acceptable salts thereof.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, and amides, salts of esters or amides, and N-oxides of a parent compound.

As used herein, the term "active ingredient" refers to a therapeutic agent and includes any substance, other than food, used in the prevention, diagnosis, alleviation, treatment, or cure of a disease or disorder. Stedman's Medical Dictionary, 25th Edition (1990). The substance can be taken by mouth; injected into a muscle, the skin, a blood vessel, or a cavity of the body; or topically applied. Mosby's Medical, Nursing & Allied Health Dictionary, 5th Edition (1998). The agent can include any substance disclosed in at least one of: The Merck Index, 14th Edition (2006); Pei-Show Juo, Concise Dictionary of Biomedicine and Molecular Biology, (1996); U.S. Pharmacopeia Dictionary, 2000 Edition; Physician's Desk Reference, 2010 Edition; Orange Book: Approved Drug Products with Therapeutic Equivalence Evaluations (April 2013); and Approved Animal & Veterinary Drug Products (Green Book) (January 2013). The term active ingredient includes, e.g., prescription and over the counter active pharmaceutical ingredients (e.g., small molecules, macrocycles, peptides, etc.), vitamins, nutraceuticals, supplements (e.g., dietary, nutritional, and herbal), cosmetics, and biologicals.

The term "pharmaceutically acceptable carrier" refers to sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include, but is not limited to, water, ethanol, polyols (such as glycerol, propylene glycol, polyethylene glycol and the like) carboxymethylcellulose and suitable mixtures thereof, vegetable oils (such as olive oil) and injectable organic esters such as ethyl oleate. Proper fluidity can be maintained, for example, by the use of coating material such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can be also be desirable to include isotonic agent such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular employed, the rate of drug release can be controlled. Depot injectable formulations are also prepared by entrapping the drug in liposomes or microemulsions which are compatible with body tissues. The injectable formulations can be sterilized, for examples, by filtration through a bacterial-retaining filter of by incorporating sterilizing agents in the form of sterile solid compositions that can be dissolved or dispersed in sterile water or other sterile injectable media just prior to use. Suitable inert carriers can include sugars such as lactose. In a particular embodiment, at least 95% by weight of the particles of the active ingredient have an effective particle size in the range of 0.01 to 10 micrometers.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B—F, C-D, C-E, and C—F are considered disclosed. Likewise, any subset or combination of these is also disclosed. Thus, for example, the sub-group of A-E, B-F, and C-E would be considered disclosed. This concept applies to all embodiments of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Crystalline Polymorphs

In an embodiment, disclosed are crystalline polymorphs of 5-aza-4'-thio-2'-deoxycytidine, wherein the crystalline polymorph has a powder X-ray diffraction pattern that contains peaks at about 8°, about 13°, about 15°, about 17°, about 19°, about 22°, about 230 about 26°, about 28°, about 29°, about 31°, about 33°, and about 37° 2θ. In a further embodiment, the crystalline polymorph has an X-ray powder diffraction pattern that is substantially similar to, or the same as, the X-ray powder diffraction pattern shown in FIG. 11.

In an embodiment, disclosed are crystalline polymorphs of 5-aza-4'-thio-2'-deoxycytidine, wherein the crystalline polymorph has a powder X-ray diffraction pattern that contains peaks at about 6°, about 12°, about 13°, about 14°, about 16°, about 18°, about 20°, about 21°, about 22°, about 26°, about 27°, about 29°, about 30°, about 33°, about 35°, about 36°, about 39°, and about 41° 2θ. In a further embodiment, the crystalline polymorph has an X-ray powder diffraction pattern substantially similar to, or the same as, the X-ray powder diffraction pattern shown in FIG. 16.

In an embodiment, the present disclosure provides an aza-T-dCyd compound consisting of a crystalline polymorph which has an X-ray powder diffraction pattern that contains peaks at about 8°, about 13°, about 15°, about 170, about 19°, about 22°, about 230 about 26°, about 28°, about 29°, about 31°, about 33°, and about 37° 2θ. In a further embodiment, the crystalline polymorph has an X-ray powder diffraction pattern that is substantially similar to, or the same as, the X-ray powder diffraction pattern shown in FIG. 11.

In an embodiment, the present disclosure provides an aza-T-dCyd compound consisting of a crystalline polymorph which has an X-ray powder diffraction pattern that contains peaks at about 6°, about 12°, about 13°, about 14°, about 16°, about 18°, about 20°, about 21°, about 22°, about 26°, about 27°, about 29°, about 30°, about 33°, about 35°, about 36°, about 39°, and about 41° 2θ. In a further embodiment, the crystalline polymorph has an X-ray powder diffraction pattern substantially similar to, or the same as, the X-ray powder diffraction pattern shown in FIG. 16.

In various embodiments, the crystalline polymorph is present in a pharmaceutical composition, together with a pharmaceutically acceptable carrier.

C. Methods of Making Crystalline Polymorphs

In an embodiment, disclosed are methods of making a disclosed crystalline polymorph, the method comprising subjecting aza-T-dCyd to one or more of solvent equilibration, evaporative crystallization, anti-solvent addition, thermocycling crystallizaiton, sonication, and vapor diffusion into solution. In a further embodiment, the crystalline polymorph has a powder X-ray diffraction pattern that contains peaks at about 8°, about 13°, about 15°, about 17°, about 19°, about 22°, about 23° about 26°, about 28°, about 29°, about 31°, about 33°, and about 37° 2θ. In a further embodiment, the crystalline polymorph has a powder X-ray diffraction pattern that contains peaks at about 6°, about 12°, about 13°, about 14°, about 16°, about 18°, about 20°, about 21°, about 22°, about 26°, about 27°, about 29°, about 30°, about 33°, about 35°, about 36°, about 39°, and about 41° 2θ.

In an embodiment, the method comprises one and only one of solvent equilibration, evaporative crystallization, anti-solvent addition, thermocycling crystallization, sonication, and vapor diffusion into solution. In an embodiment, the method comprises exactly two of solvent equilibration, evaporative crystallization, anti-solvent addition, thermocycling crystallization, sonication, and vapor diffusion into solution. In an embodiment, the method comprises more than two of solvent equilibration, evaporative crystallization, anti-solvent addition, thermocycling crystallization, sonication, and vapor diffusion into solution.

D. Pharmaceutical Compositions

The present disclosure provides compositions comprising crystalline polymorphs of aza-T-dCyd. Such compositions include pharmaceutical compositions comprising a therapeutically effective amount of crystalline polymorphs of aza-T-dCyd and a pharmaceutically acceptable carrier. Generally, all known or approved amounts of crystalline aza-T-dCyd can be used in the composition. In an embodiment, the crystalline aza-T-dCyd is in Form A or Form F and is present in an amount of about 30 $mg/m^2$ to about 70 $mg/m^2$. In a particular embodiment, the crystalline polymorphs of aza-T-dCyd is present at an amount of about 35 $mg/m^2$ to about 45 $mg/m^2$, about 45 $mg/m^2$ to about 55 $mg/m^2$, or about 55 $mg/m^2$ to about 66 $mg/m^2$.

In an embodiment, disclosed are pharmaceutical compositions comprising an effective amount of: (a) a crystalline polymorph having a powder X-ray diffraction pattern that contains peaks at about 8°, about 13°, about 15°, about 17°, about 19°, about 22°, about 23° about 26°, about 28°, about 29°, about 31°, about 33°, and about 37° 2θ; or (b) a crystalline polymorph having a powder X-ray diffraction pattern that contains peaks at about 6°, about 12°, about 13°, about 14°, about 16°, about 18°, about 20°, about 21°, about 22°, about 26°, about 27°, about 29°, about 30°, about 33°, about 35°, about 36°, about 39°, and about 41° 2θ, and a pharmaceutically acceptable carrier. In a further embodiment, the crystalline polymorph has a powder X-ray diffraction pattern that contains peaks at about 8°, about 13°, about 15°, about 17°, about 19°, about 22°, about 23° about 26°, about 28°, about 29°, about 31°, about 33°, and about 37° 2θ. In a still further embodiment, the crystalline polymorph has a powder X-ray diffraction pattern that contains peaks at about 6°, about 12°, about 13°, about 14°, about 16°, about 18°, about 20°, about 21°, about 22°, about 26°, about 27°, about 29°, about 30°, about 33°, about 35°, about 36°, about 39°, and about 41° 2θ.

In an embodiment, the effective amount is of from about 35 mg/m$^2$ to about 70 mg/m$^2$, about 35 mg/m$^2$ to about 65 mg/m$^2$, about 35 mg/m$^2$ to about 55 mg/m$^2$, about 35 mg/m$^2$ to about 45 mg/m$^2$, about 40 mg/m$^2$ to about 70 mg/m$^2$, about 50 mg/m$^2$ to about 70 mg/m$^2$, about 60 mg/m$^2$ to about 70 mg/m$^2$, about 40 mg/m$^2$ to about 65 mg/m$^2$, about 45 mg/m$^2$ to about 60 mg/m$^2$, or about 50 mg/m$^2$ to about 55 mg/m$^2$.

In an embodiment, the composition further comprises a chemotherapeutic agent. Examples of chemotherapeutic agents include, but are not limited to, an alkylating agent, an antimetabolite agent, an antineoplastic antibiotic agent, a mitotic inhibitor agent, and an mTOR inhibitor agent.

In an embodiment, the composition further comprises an alkylating agent. Examples of alkylating agents include, but are not limited to, carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or pharmaceutically acceptable salts thereof.

In an embodiment, the composition further comprises an antimetabolite agent. Examples of antimetabolite agents include, but are not limited to, gemcitabine, 5-fluorouracil, capectiabine, hydroxyurea, mercaptopurine, pemetrexed, fludarabine, nelarabine, cladribine, clofarabine, cytarabine, decitabine, pralatrexate, floxuridine, methotrexate, and thioguanine, or pharmaceutically acceptable salts thereof.

In an embodiment, the composition further comprises an antineoplastic antibiotic agent. Examples of antineoplastic antibiotic agents include, but are not limited to, doxorubicin, mitoxantrone, bleomycin, daunorubicin, epirubicin, idarubicin, plicamycin, mitomycin, pentostatin, and valrubicin, or pharmaceutically acceptable salts thereof.

In an embodiment, the composition further comprises a mitotic inhibitor agent. Examples of mitotic inhibitor agents include, but are not limited to, irinotecan, topotecan, rubitecan, cabazitaxel docetaxel, paclitaxel, etopside, vincristine, exabepilone, vinorelbine, vinblastine, and teniposide, or pharmaceutically acceptable salts thereof.

In an embodiment, the composition further comprises an mTOR inhibitor agent. Examples of mTOR inhibitor agents include, but are not limited to, everolimus, sirolimus, and temsirolimus, or pharmaceutically acceptable salts thereof.

In an embodiment, compositions comprising crystalline polymorphs of aza-T-dCyd are formulated for systemic or local administration. Formulation for oral, topical, intravenous, or intramuscular administration are contemplated. In a particular embodiment, the crystalline polymorphs of aza-T-dCyd is formulated for oral administration.

In an embodiment, the pharmaceutical composition comprises an active ingredient consisting of a crystalline polymorph having a powder X-ray diffraction pattern that contains peaks at about 8°, about 13°, about 15°, about 170, about 19°, about 22°, about 23θ about 26°, about 28°, about 29°, about 31°, about 33°, and about 37° 2θ.

In an embodiment, the pharmaceutical composition comprises an active ingredient consisting of a crystalline polymorph having a powder X-ray diffraction pattern that contains peaks at about 6°, about 12°, about 13°, about 14°, about 16°, about 18°, about 20°, about 21°, about 22°, about 26°, about 27°, about 29°, about 30°, about 33°, about 35°, about 36°, about 39°, and about 41° 2θ.

In an embodiment, the pharmaceutical composition comprises a crystalline polymorph having a powder X-ray diffraction pattern that contains peaks at about 8°, about 13°, about 15°, about 17°, about 19°, about 22°, about 23° about 26°, about 28°, about 29°, about 31°, about 33°, and about 37° 2θ, but does not comprise other crystalline polymorphs of aza-T-dCyd.

In an embodiment, the pharmaceutical composition comprises a crystalline polymorph having a powder X-ray diffraction pattern that contains peaks at about 6°, about 12°, about 13°, about 14°, about 16°, about 18°, about 20°, about 21°, about 22°, about 26°, about 27°, about 29°, about 30°, about 33°, about 35°, about 36°, about 39°, and about 41° 2θ, but does not comprise other crystalline polymorphs of aza-T-dCyd.

In a particular embodiment, the composition comprises any convenient pharmaceutical media. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

E. Methods of Using the Crystalline Polymorphs and Compositions Containing Same The crystalline polymorphs and pharmaceutical compositions of the invention are useful in treating or controlling cancers such as blood cancer (e.g., non-Hodgkin's lymphoma, Hodgkin's lymphoma, multiple myeloma, leukemia, lymphoma, myelodysplastic syndrome, acute lymphocytic leukemia, acute myelogenous leukemia, chronic lymphocytic leukemia, chronic myeloid leukemia, and solitary myeloma) and solid tumors (e.g., stomach cancer, kidney cancer, ovarian cancer, cervical cancer, uterine cancer, prostate cancer, lung cancer, colon cancer, breast cancer, melanoma, and pancreatic cancer).

To treat or control the cancer, the crystalline polymorphs and pharmaceutical compositions comprising the crystalline polymorphs are administered to a subject in need thereof, such as a vertebrate, e.g., a mammal, a fish, a bird, a reptile, or an amphibian. The subject can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. The subject is preferably a mammal, such as a human. Prior to administering the crystalline polymorphs or compositions, the subject can be diagnosed with a need for treatment of cancer, such as, for example, a blood cancer or solid tumor.

The crystalline polymorphs or compositions can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of a cancer, such as a blood cancer or a solid tumor.

The therapeutically effective amount or dosage of the crystalline polymorph can vary within wide limits. Such a dosage is adjusted to the individual requirements in each particular case including the specific compound(s) being administered, the route of administration, the condition being treated, as well as the patient being treated. In general, in the case of oral or parenteral administration to adult humans weighing approximately 70 Kg or more, a daily dosage of about 10 mg to about 10,000 mg, preferably from about 200 mg to about 1,000 mg, should be appropriate, although the upper limit may be exceeded. The daily dosage can be administered as a single dose or in divided doses, or for parenteral administration, as a continuous infusion. Single dose compositions can contain such amounts or submultiples thereof of the compound or composition to make up the daily dose. The dosage can be adjusted by the individual physician in the event of any contraindications. Dosage can vary, and can be administered in one or more dose administrations daily, for one or several days.

1. Treatment Methods

The crystalline polymorphs disclosed herein are useful for treating or controlling cancers such as blood cancer (e.g., non-Hodgkin's lymphoma, Hodgkin's lymphoma, multiple myeloma, leukemia, lymphoma, myelodysplastic syndrome, acute lymphocytic leukemia, acute myelogenous leukemia, chronic lymphocytic leukemia, chronic myeloid leukemia, and solitary myeloma) and solid tumors (e.g., stomach cancer, kidney cancer, ovarian cancer, cervical cancer, uterine cancer, prostate cancer, lung cancer, colon cancer, breast cancer, melanoma, and pancreatic cancer). Thus, provided is a method comprising administering a therapeutically effective amount of a disclosed crystalline polymorph, or a composition comprising a disclosed crystalline polymorph, to a subject. In a further aspect, the method can be a method for treating cancer.

a. Treating Cancer

The present disclosure provides various methods of using the aza-T-dCyd composition for the treatment of disease(s) such as cancer. In an embodiment, the crystalline polymorph of aza-T-dCyd is administered to a subject to treat a blood cancer, wherein the subject is in need of such treatment. Various blood cancers can be treated by the composition and in some embodiments, the blood cancer is selected from the group consisting of non-Hodgkin's lymphoma, Hodgkin's lymphoma, multiple myeloma, leukemia, lymphoma, myelodysplastic syndrome, acute lymphocytic leukemia, acute myelogenous leukemia, chronic lymphocytic leukemia, chronic myeloid leukemia, and solitary myeloma. In a specific embodiment, a therapeutically effective amount of the crystalline polymorph of aza-T-dCyd is administered with an additional chemotherapeutic agent, such as an alkylating agent, an antimetabolite agent, an antineoplastic antibiotic agent, a mitotic inhibitor agent, or an mTOR inhibitor agent Thus, in an embodiment, disclosed are methods of treating a cancer in a subject in need thereof, the method comprising administering to the subject an effective amount of a crystalline polymorph having a powder X-ray diffraction pattern that contains peaks at about 8°, about 13°, about 15°, about 17°, about 19°, about 22°, about 23° about 26°, about 28°, about 29°, about 31°, about 33°, and about 37° 2θ.

In an embodiment, disclosed are methods of treating a cancer in a subject in need thereof, the method comprising administering to the subject an effective amount of a crystalline polymorph having a powder X-ray diffraction pattern that contains peaks at about 6°, about 12°, about 13°, about 14°, about 16°, about 18°, about 20°, about 21°, about 22°, about 26°, about 27°, about 29°, about 30°, about 33°, about 35°, about 36°, about 39°, and about 41° 2θ.

In an embodiment, disclosed are methods of treating a cancer in a subject in need thereof, the method comprising administering to the subject an effective amount of an aza-T-dCyd compound consisting of a crystalline polymorph having a powder X-ray diffraction pattern that contains peaks at about 8°, about 13°, about 15°, about 17°, about 19°, about 22°, about 23° about 26°, about 28°, about 29°, about 31°, about 33, and about 37° 2θ.

In an embodiment, disclosed are methods of treating a cancer in a subject in need thereof, the method comprising administering to the subject an effective amount of an aza-T-dCyd compound consisting of a crystalline polymorph having a powder X-ray diffraction pattern that contains peaks at about 6°, about 12°, about 13°, about 14°, about 16°, about 18°, about 20°, about 21°, about 22°, about 26°, about 27°, about 29°, about 30°, about 33°, about 35°, about 36°, about 39°, and about 41° 2θ.

In an embodiment, the cancer is a blood cancer. Examples of blood cancers include, but are not limited to, non-Hodgkin's lymphoma, Hodgkin's lymphoma, multiple myeloma, leukemia, lymphoma, myelodysplastic syndrome, acute lymphocytic leukemia, acute myelogenous leukemia, chronic lymphocytic leukemia, chronic myeloid leukemia, and solitary myeloma.

In an embodiment, the cancer is a solid tumor. Examples of solid tumors include, but are not limited to, stomach cancer, kidney cancer, ovarian cancer, cervical cancer, uterine cancer, prostate cancer, lung cancer, colon cancer, breast cancer, melanoma, and pancreatic cancer.

In an embodiment, the effective amount is a therapeutically effective amount. In a further embodiment, the effective amount is of from about 35 mg/m$^2$ to about 70 mg/m$^2$, about 35 mg/m$^2$ to about 65 mg/m$^2$, about 35 mg/m$^2$ to about 55 mg/m$^2$, about 35 mg/m$^2$ to about 45 mg/m$^2$, about 40 mg/m$^2$ to about 70 mg/m$^2$, about 50 mg/m$^2$ to about 70 mg/m$^2$, about 60 mg/m$^2$ to about 70 mg/m$^2$, about 40 mg/m$^2$ to about 65 mg/m$^2$, about 45 mg/m$^2$ to about 60 mg/m$^2$, or about 50 mg/m$^2$ to about 55 mg/m$^2$.

In an embodiment, the crystalline polymorph is present in a pharmaceutical composition.

In an embodiment, the method further comprises administering a chemotherapeutic agent to the subject.

In an embodiment, the effective amount is administered in a single dose. In a further embodiment, the effective amount is administered via a plurality of doses.

In an embodiment, the method further comprises identifying a subject in need of treatment of blood cancer. In a further embodiment, the subject has been diagnosed with a need for treatment of cancer prior to the administering step.

In an embodiment, administering is repeated administration. In a further embodiment, administering is for a time period of from about 4 days to about 6 days, about 4 days to about 5 days, or about 5 days to about 6 days. In a still further embodiment, administering is for a time period of about 5 days.

In an embodiment, administering is via a treatment cycle. In a further embodiment, each treatment cycle includes administering the effective amount of the compound for a time period of from about 4 days to about 6 days.

In an embodiment, administering is via a course of treatment comprising a plurality of treatment cycles and a plurality of rest periods. In a further embodiment, each treatment cycle includes administering the effective amount of the compound for a time period of from about 4 days to about 6 days. In a still further embodiment, each treatment cycle includes administering the effective amount of the compound for a time period of about 5 days. In yet a further embodiment, each rest period includes abstaining from administering the compound for a time period of from about 1 day to about 10 days.

In an embodiment, administering is via a course of treatment comprising: a first treatment cycle that includes administering the effective amount of the crystalline polymorph for a time period of from about 4 days to about 6 days; a first rest period that includes abstaining from administering the crystalline polymorph for a time period of about 1 day to about 3 days; a second treatment cycle that includes administering the effective amount of the crystalline polymorph for a time period of from about 4 days to about 6 days; and a second rest period that includes abstaining from administering the crystalline polymorph for a time period of at least about 8 days. In a further embodiment, the effective amount is administered in a single dose. In a still further embodiment, the effective amount is administered via a plurality of doses. In yet a further embodiment, the effective amount is administered via a single dose on some days and via a plurality of doses on other days.

In an embodiment, administering is via a course of treatment comprising: a first treatment cycle that includes administering the effective amount of the crystalline polymorph for a time period of about 5 days; a first rest period that includes abstaining from administering the crystalline polymorph for a time period of about 2 days; a second treatment cycle that includes administering the effective amount of the crystalline polymorph for a time period of about 5 days; and a second rest period that includes abstaining from administering the crystalline polymorph for a time period of at least about 9 days.

In an embodiment, the subject is diagnosed as having a blood cancer, wherein the diagnosis can be made prior to administration of the crystalline polymorph of aza-T-dCyd. In an embodiment, the crystalline polymorph of aza-T-dCyd is administered in a single dose or over a plurality of doses. In a specific embodiment, the crystalline polymorph of aza-T-dCyd is administered over repeated administrations, such as in a treatment cycle. In a particular embodiment, the aza-T-dCyd is administered over the course of about 4 to about 6 days. In a particular embodiment, the crystalline polymorph of aza-T-dCyd is administered via a course of treatment comprising: a first treatment cycle comprising administering the therapeutically effective amount of the crystalline polymorph over the course of about 4 to about 6 days; a first rest period of about 1 to about 3 days during which the crystalline polymorph is not administered; a second treatment cycle comprising administering the therapeutically effective amount of the crystalline polymorph over the course of about 4 to about 6 days; and a second rest period of at least about 8 days during which the crystalline polymorph is not administered. In a still further embodiment, crystalline polymorph of aza-T-dCyd is administered via a course of treatment comprising: a first treatment cycle comprising administering the therapeutically effective amount of the crystalline polymorph over the course of about 5 days; a first rest period of about 2 days during which the crystalline polymorph is not administered; a second treatment cycle comprising administering the therapeutically effective amount of the crystalline polymorph over the course of about 5 days; and a second rest period of at least about 9 days during which the crystalline polymorph is not administered.

2. Use of Compounds and Compositions

In an embodiment, the invention relates to the use of a disclosed composition. In a further embodiment, a use relates to the manufacture of a medicament for the treatment of a blood cancer in a subject.

In an embodiment, the use relates to a process for preparing a disclosed pharmaceutical composition for use as a medicament.

In an embodiment, the use relates to a process for preparing a disclosed pharmaceutical composition, wherein a pharmaceutically acceptable carrier is intimately mixed with a therapeutically effective amount of the compound.

In various embodiments, the use relates to a treatment of a blood cancer in a subject. In one embodiment, the use is characterized in that the subject is a human. In one embodiment, the use is characterized in that the blood cancer is non-Hodgkin's lymphoma, Hodgkin's lymphoma, multiple myeloma, leukemia, lymphoma, myelodysplastic syndrome, acute lymphocytic leukemia, acute myelogenous leukemia, chronic lymphocytic leukemia, chronic myeloid leukemia, or solitary myeloma.

In a further embodiment, the use relates to the manufacture of a medicament for the treatment of a blood cancer in a subject. In one embodiment, the use is characterized in that the blood cancer is non-Hodgkin's lymphoma, Hodgkin's lymphoma, multiple myeloma, leukemia, lymphoma, myelodysplastic syndrome, acute lymphocytic leukemia, acute myelogenous leukemia, chronic lymphocytic leukemia, chronic myeloid leukemia, or solitary myeloma.

3. Manufacture of a Medicament

In an embodiment, the invention relates to a method for the manufacture of a medicament for treating a blood cancer in a human subject having the blood cancer, the method comprising combining a therapeutically effective amount of a disclosed compound with a pharmaceutically acceptable carrier or diluent.

As regards these applications, the present method includes the administration to a human of a therapeutically effective amount of the composition. The dose administered to a human, in the context of the present invention, should be sufficient to affect a therapeutic response in the human over a reasonable time frame. One skilled in the art will recognize that dosage will depend upon a variety of factors including the condition of the human and the body weight of the human.

The total amount of the composition of the present disclosure administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the composition and the desired physiological effect. It will be appreciated by one of skill in the art that various conditions or disease states, in particular chronic conditions or disease states, may require prolonged treatment involving multiple administrations.

Thus, in an embodiment, the invention relates to the manufacture of a medicament comprising combining a disclosed compound, or a pharmaceutically acceptable salt, solvate, or polymorph thereof, with a pharmaceutically acceptable carrier or diluent.

4. Kits

In an embodiment, disclosed are kits comprising an effective amount of a disclosed crystalline polymorph, and one or more of: (a) at least one chemotherapeutic agent; (b) instructions for administering the composition in connection with treating cancer; and (c) instructions for treating cancer. In a further embodiment, the crystalline polymorph has a powder X-ray diffraction pattern that contains peaks at about 8°, about 13°, about 15°, about 17°, about 19°, about 22°, about 230 about 26°, about 28°, about 29°, about 31°, about 33°, and about 37° 2θ. In a still further embodiment, the crystalline polymorph has a powder X-ray diffraction pattern that contains peaks at about 6°, about 12°, about 13°, about 14°, about 16°, about 18°, about 20°, about 21°, about 22°, about 26°, about 27°, about 29°, about 30°, about 33°, about 35°, about 36°, about 39°, and about 41° 2θ.

In an embodiment, the agent is a chemotherapeutic agent. Examples of chemotherapeutic agents include, but are not limited to, alkylating agents, antimetabolite agents, antineoplastic antibiotic agents, mitotic inhibitor agents, and mTor inhibitor agents.

In an embodiment, the chemotherapeutic agent is an alkylating agent. Examples of alkylating agents include, but are not limited to carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt thereof.

In an embodiment, the chemotherapeutic agent is an antimetabolite agent. Examples of antimetabolite agents include, but are not limited to, gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt thereof.

In an embodiment, the chemotherapeutic agent is an antineoplastic antibiotic agent. Examples of antineoplastic antibiotic agents include, but are not limited to doxorubicin, mitoxantrone, bleomycin, daunorubicin, dactinomycin, epirubicin, idarubicin, plicamycin, mitomycin, pentostatin, and valrubicin, or a pharmaceutically acceptable salt thereof.

In an embodiment, the chemotherapeutic agent is a mitotic inhibitor agent. Examples of mitotic inhibitor agents include, but are not limited to, irinotecan, topotecan, rubitecan, cabazitaxel, docetaxel, paclitaxel, etoposide, vincristine, ixabepilone, vinorelbine, vinblastine, and teniposide, or a pharmaceutically acceptable salt thereof.

In an embodiment, the chemotherapeutic agent is an mTor inhibitor agent. Examples of mTor inhibitor agents include, but are not limited to, everolimus, siroliumus, and temsirolimus, or a pharmaceutically acceptable salt, hydrate, solvate, or polymorph thereof.

In various embodiments, the crystalline polymorph and the agent are co-packaged. In various further embodiments, the crystalline polymorph and the agent are co-formulated.

In various further embodiments, the crystalline polymorph and the agent are administered sequentially. In various further embodiments, the crystalline polymorph and the agent are administered simultaneously.

In various embodiments, the disorder of uncontrolled cellular proliferation is a cancer. In various further embodiments, the cancer is a blood cancer.

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

F. Examples

1. Preparation Methods a. Anti-Solvent Addition

The anti-solvent crystallization experiments were performed by combining 10 different solvents with 10 anti-solvents. The anti-solvent crystallization experiments were performed by reverse addition in which a small amount of a near saturated solution of the aza-T-dCyd in the selected solvent was added to 20 mL of anti-solvent, which was vigorously agitated.

The samples in which no precipitation occurred were placed at 5° C. for 3 days to induce precipitation. The precipitated solids were isolated from the mother liquor and analyzed by HT-XRPD after drying in a glovebox (20% RH) overnight and after drying under vacuum (10 mbar) overnight. All solids were exposed to accelerated aging conditions (2 days at 25° C./60% RH) and re-analyzed by HT-XRPD.

b. Evaporative Crystallization

For the evaporative crystallization experiments from solvent mixtures, new solutions were prepared from the crystalline starting material. The solutions were transferred to vials (without caps) and left in glovebox conditions (20% RH/RT) to allow the solvents to evaporate slowly for 3 days, followed by vacuum (10 mbar) at RT until all solvent was evaporated. The samples with NMP (Exp. ID ECP43 and ECP44) were further dried under vacuum at 50° C. The obtained solids were analyzed by HT-XRPD. Subsequently, the solids were placed at 25° C./60% RH for two days (AAC) and re-analyzed by XRPD.

c. Solvent Equilibration

The solvent equilibration experiments were performed in 29 solvents. To about 20 mg of aza-T-dCyd, the solvents were added in small steps until a thin suspension was obtained. The suspensions were left to equilibrate with continuous stirring for 5 days at 5° C. and 1 day at 25° C.

After the equilibration time (1 day at RT and 5 days at 5° C.), the solids were separated by centrifugation. A part of the solids was collected and harvested on a 96 well plate and dried in a glovebox (with relative humidity of 20% at RT) overnight. The remaining solids were dried under vacuum (RT and 10 mbar) overnight and then harvested on a 96 well plate. All solids were analyzed by HT-XRPD. Subsequently, all solids were exposed to accelerated aging conditions for two days (AAC, 25° C./60% RH) and re-analyzed by HT-XRPD.

d. Sonication

The sonication experiments were started with the crystalline aza-T-dCyd. About 20 mg of API was weighed in 1.8 mL vials and 5-10 µL of solvent was added until a paste was obtained. The pastes were sonicated at RT for 10 minutes in an ultrasonic bath (Fisher Scientific, FB15051). The solids were harvested and analyzed by HT-XRPD and re-analyzed after drying under vacuum (10 mbar/RT overnight). Subsequently, all the solids were exposed to accelerated aging conditions (25° C./60% RH) for two days and re-analyzed by HT-XRPD.

e. Thermocycling Crystallization

The thermocycling crystallization experiments were performed in 20 organic solvents and solvent mixtures. To about 25 mg of aza-T-dCyd small aliquots of solvent (mixture) was added until a thin suspension was obtained at room temperature. Subsequently, the mixtures were placed in the Crystal 16™ reactors to undergo a temperature profile as displayed in FIG. 16. Samples were heated to 50° C. and cooled to 5° C. with a heating and cooling rate of 10° C./h and after 3 cycles aged at RT for 24 hours.

After the temperature profile the solids were separated from the solution by centrifugation, a part was dried in a glovebox (20% RH) at RT and a part was dried under deep vacuum (10 mbar) before being harvested and analyzed by HT-XRPD. The liquid phases were also evaporated and recovered solids were analyzed by HT-XRPD. All solids were then exposed to accelerated aging conditions (2 days at 25° C./60% RH) followed by HT-XRPD re-analysis.

f. Vapor Diffusion

The vapor diffusion into solution experiments were performed at RT. Near saturated solutions of the aza-T-dCyd were prepared in the solvents in 1.8 mL glass vials or 40 mL vials. The open vials containing the saturated solution were placed in a closed bigger vial containing 2-5 mL of antisolvent. The samples were checked for solid formation after one week. The solids were analyzed by HT-XRPD after drying in a glovebox (20% RH) and after drying under vacuum (10 mbar). If no precipitation occurred, the solvent was evaporated under vacuum and the resulting solids analyzed by HT-XRPD. Subsequently, all solids were exposed to accelerated aging conditions (2 days at 25° C./60% RH) and re-analyzed by HT-XRPD.

2. Analytical Methods a. HT-XRPD

XRPD patterns were obtained using the Ardena SSR T2 high-throughput XRPD set-up. The plates were mounted on a Bruker General Area Detector Diffraction System (GADDS) equipped with a VÅNTEC-500 gas area detector corrected for intensity and geometric variations. The calibration of the measurement accuracy (peaks position) was performed using NIST SRM1976 standard (Corundum).

Data collection was carried out at room temperature using monochromatic CuKα radiation in the 2 Å region between 1.5° and 41.5°, which is the most distinctive part of the XRPD pattern. The diffraction pattern of each well was collected in two 2θ ranges (1.5°≤2θ≤21.5° for the first frame, and 19.5°≤2θ≤41.5° for the second) with an exposure time of 90 s for each frame. No background subtraction or curve smoothing was applied to the XRPD patterns.

The carrier material used during XRPD analysis was transparent to X-rays and contributed only slightly to the background.

b. HR-XRPD

The HR-XRPD data were collected on D8 Advance diffractometer using Cu Kα1 radiation (1.54056 Å) with germanium monochromator at RT. Diffraction data were collected in the 2θ range 2-41.5° 2θ. Detector scan on solid state LynxEye detector was performed using 0.0160 per step with 5 sec/step scan speed. The samples were measured in 8 mm long glass capillary with 0.5 mm outer diameter.

c. TGMS Analysis

Mass loss due to solvent or water loss from the crystals was determined by TGA. Monitoring the sample weight, during heating in a TGA/DSC 3+ STARe system (Mettler-Toledo GmbH, Switzerland), resulted in a weight vs. temperature curve and a heat flow thermogram. The TGA/DSC 3+ was calibrated for temperature with indium and aluminum. Samples (circa 2 mg) were weighed into 100 µL aluminum crucibles and sealed. The seals were pin-holed, and the crucibles heated in the TGA from 25 to 300° C. at a heating rate of 10° C./min. Dry $N_2$ gas was used for purging.

The gases evolved from the TGA samples were analyzed by an Omnistar GSD 301 T2 mass spectrometer (Pfeiffer Vacuum GmbH, Germany). This MS is a quadrupole mass spectrometer, which analyses masses in the range of 0-200 amu.

d. DSC Analysis

Thermal events (i.e., melting, re-crystallization) were obtained from DSC thermograms, recorded with a heat flux DSC3+ STARe system (Mettler-Toledo GmbH, Switzerland). The DSC3+ was calibrated for temperature and enthalpy with a small piece of indium (m.p.=156.6° C.; δHf=28.45 J/g) and zinc (m.p.=419.6° C.; δHf=107.5 J/g). Samples (circa 2 mg) were sealed in standard 40 µL aluminum pans, pin-holed and heated in the DSC from 25° C. to 300° C., at a heating rate of 10° C./min. Dry $N_2$ gas, at a flow rate of 50 mL/min was used to purge the DSC equipment during measurement.

The cycling DSC experiments were measured in standard 40 µL aluminum pans, pin-holed and heated in the DSC from 25° C. to variable temperatures, then cooled back to 25° C. The heating and cooling rate was 10° C./min. Dry N2 gas, at a flow rate of 50 mL/min was used to purge the DSC equipment during measurement. Afterwards the samples were recovered and analyzed by HT-XRPD.

e. LCMS

LCMS experiments were performed on an Agilent 1290 series machine with diode array UV detector and MSD XT single quad mass detector. Mobile phases A and B are 10 mM ammonium acetate in water and acetonitrile, respectively. The column was a Waters XBridge HILIC (150×4.6 mm; 3.5 µm, pn. 186004441). Detection was at 244 nm, with a bandwidth of 4 nm, a UV spectrum of 200-400 nm. Spectrometry was performed in positive scan mode 100-800 m/z, 500 ms scan time. The flow rate was 0.8 mL/min. The run time was 10 minutes. Injection volume was 5 µL at 40° C., with an autosampler temperature of 8° C.

3. Example 1: Characterization of Starting Materials

Approximately 4.0 g of aza-T-dCyd was prepared and analyzed by X-ray powder diffraction (XRPD), differential scanning calorimetry (DSC), thermogravimetric analysis/mass spectrometry (TGMS) analysis, and liquid chromatography/mass spectrometry (LCMS). Starting material (SM) represents aza-T-dCyd that has not yet been subjected to specific crystallization conditions. FIG. 1 shows the high throughput XRPD (HT-XRPD) and high resolution XRPD (HR-XRPD) in the upper and lower patterns, respectively. The starting material contains crystals suitable for single crystal structure analysis. The starting material crystallized in the non-centrosymmetric monoclinic $P2_1$ space group and designated Form A. Table 1 provides the relevant dimensions of Form A.

TABLE 1

| Parameter | Value |
| --- | --- |
| a | 5.5505(3) Å |
| b | 8.4308(4) Å |
| c | 11.7738(8) Å |
| β | 100.519(2)° |
| V | 537.31(5) Å$^3$ |
| Z | 2 |
| density | 1.510 g/cm$^3$ |

Figure 2:
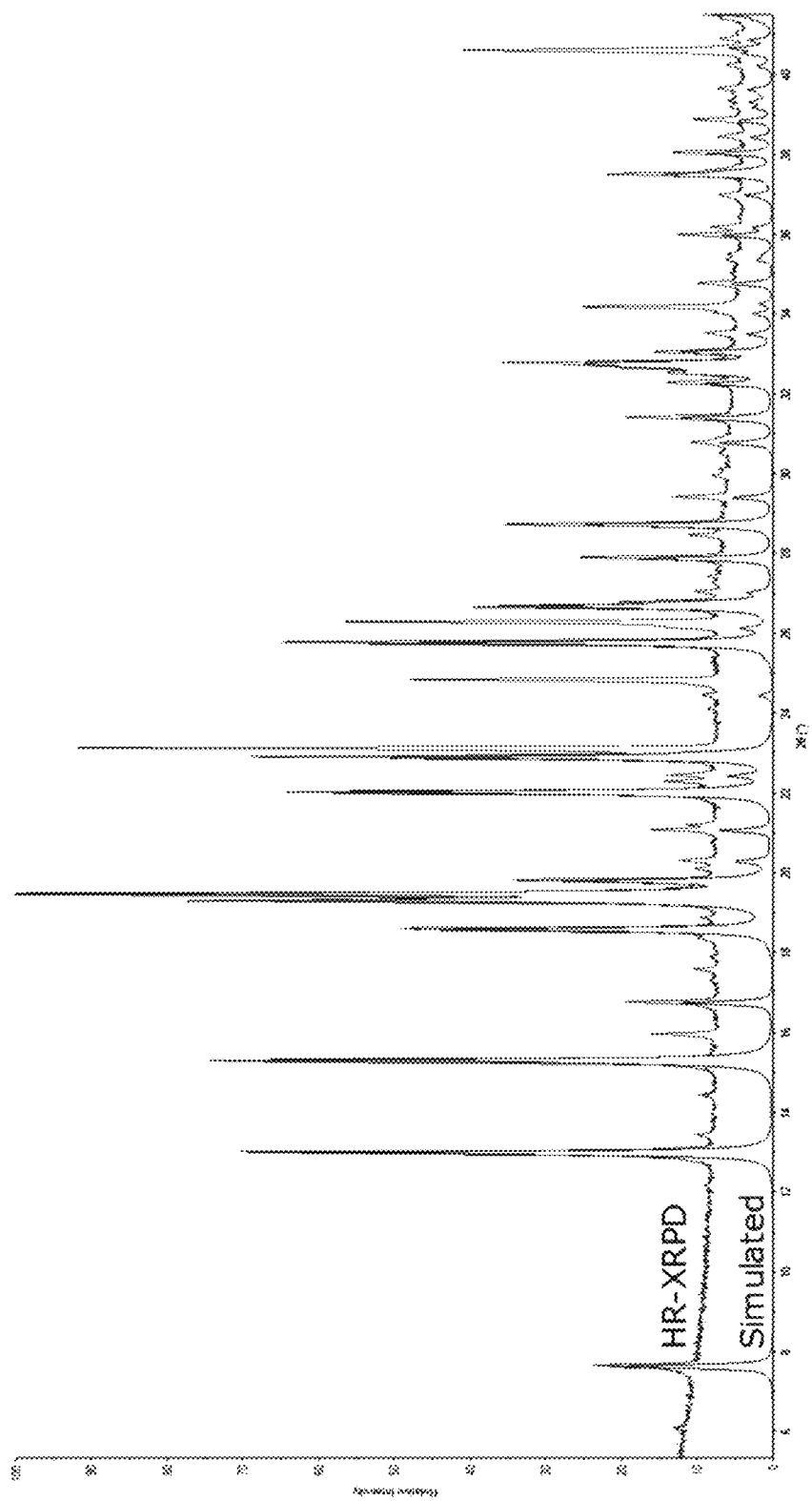
FIG. 2 shows representative simulated XRPD and HR-XRPD of aza-T-dCyd Form A.

HR-XRPD pattern of the starting material was compared to a simulated pattern HR-XRPD pattern of single crystal Form A, and shown in FIG. 2. Form A has peaks at 7.7°, 13.02°, 15.34°, 16.78°, 18.62°, 19.42°, 21.94°, 22.90°, 25.70°, 27.86°, 28.70°, 31.42°, 32.70°, and 37.46° 2θ. Based on this comparison, the starting material is calculated to comprise about 70% of Form A and about 30% of other crystalline forms of aza-T-dCyd.

Figure 3:
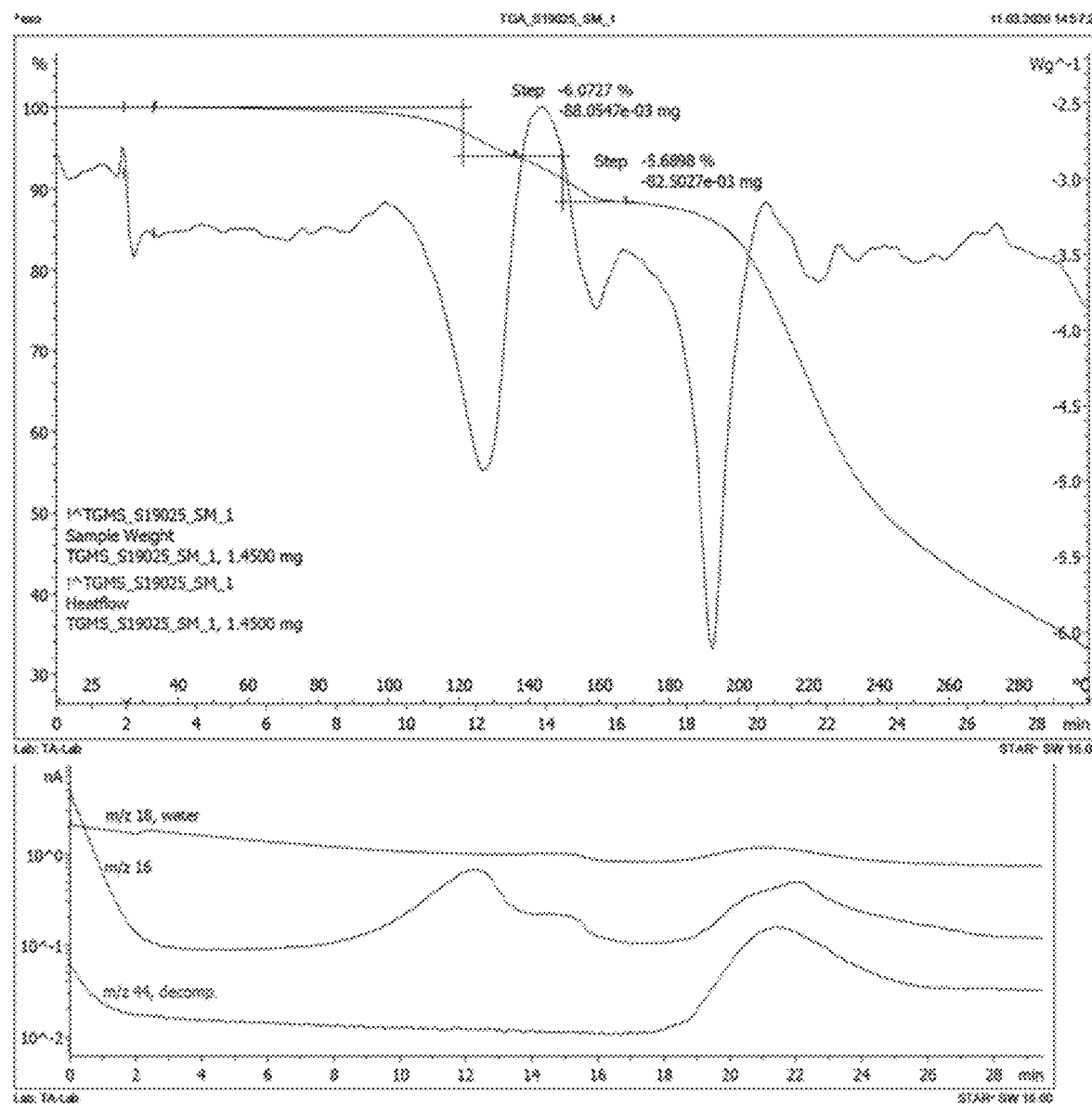
FIG. 3 shows representative TGMS analysis of aza-T-dCyd starting material (SM).

The TGMS analysis of the starting material between 25-300° C. (10° C./min) showed a mass loss of 11.7% between 100-170° C. due to most likely organic solvent (FIG. 3). Simultaneously to the mass loss, the heat flow signal showed two endothermic events, with an exothermic event in between. A third endothermic event was observed around 195° C. due to melting and starting of decomposition.

Figure 4:
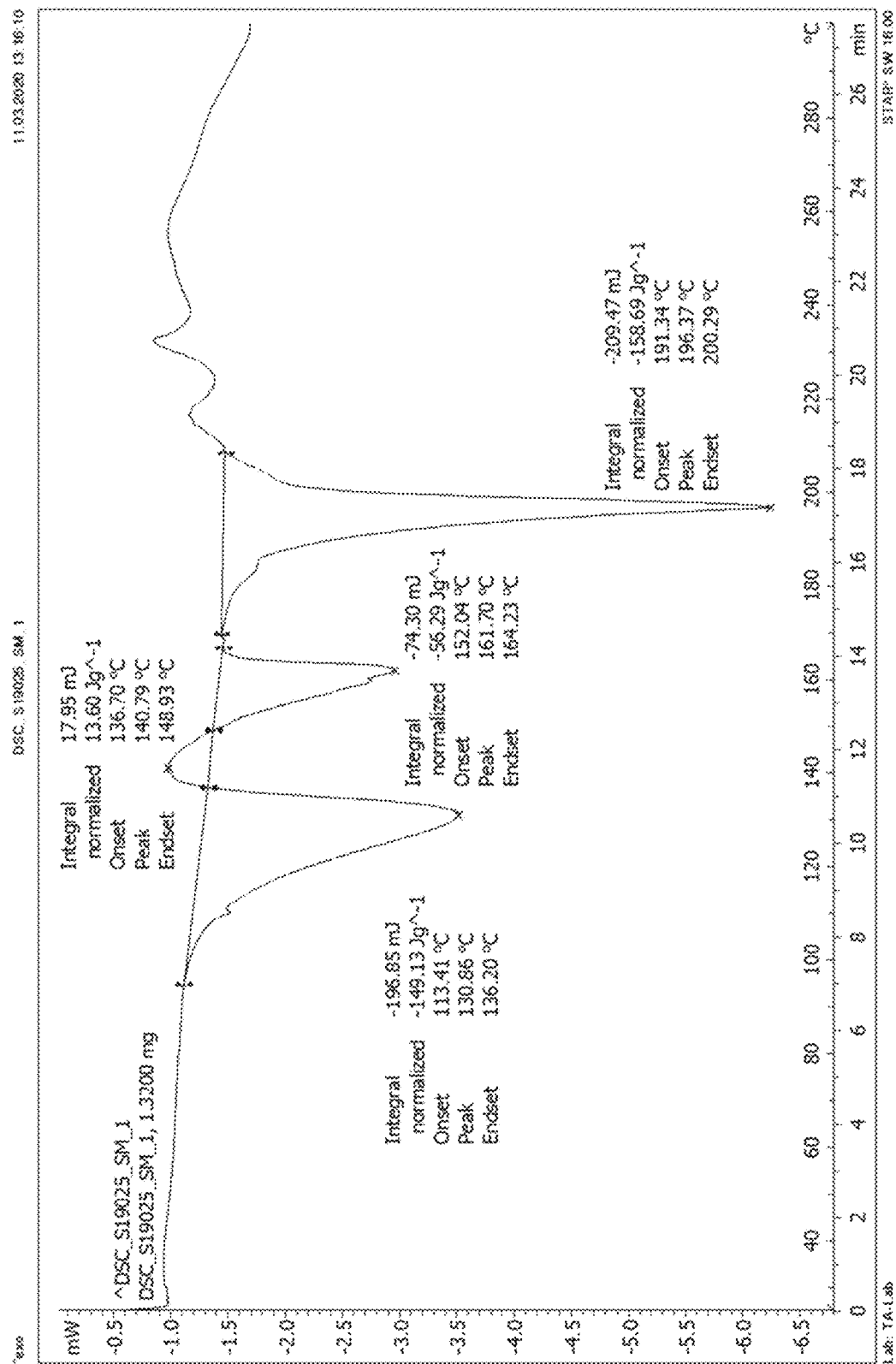
FIG. 4 shows a representative DSC trace of aza-T-dCyd starting material (SM).

The DSC analysis of the start material between 25-300° C. (10° C./min) agreed with the heat flow signal observed during TGMS analysis and showed two endothermic events at 131° C. and 162° C. with an exothermic event at 141° C. A third endothermic event was observed at $T_{peak}$ at 196.4° C., related to melting of a non-solvated anhydrous phase (FIG. 4).

Figure 5:
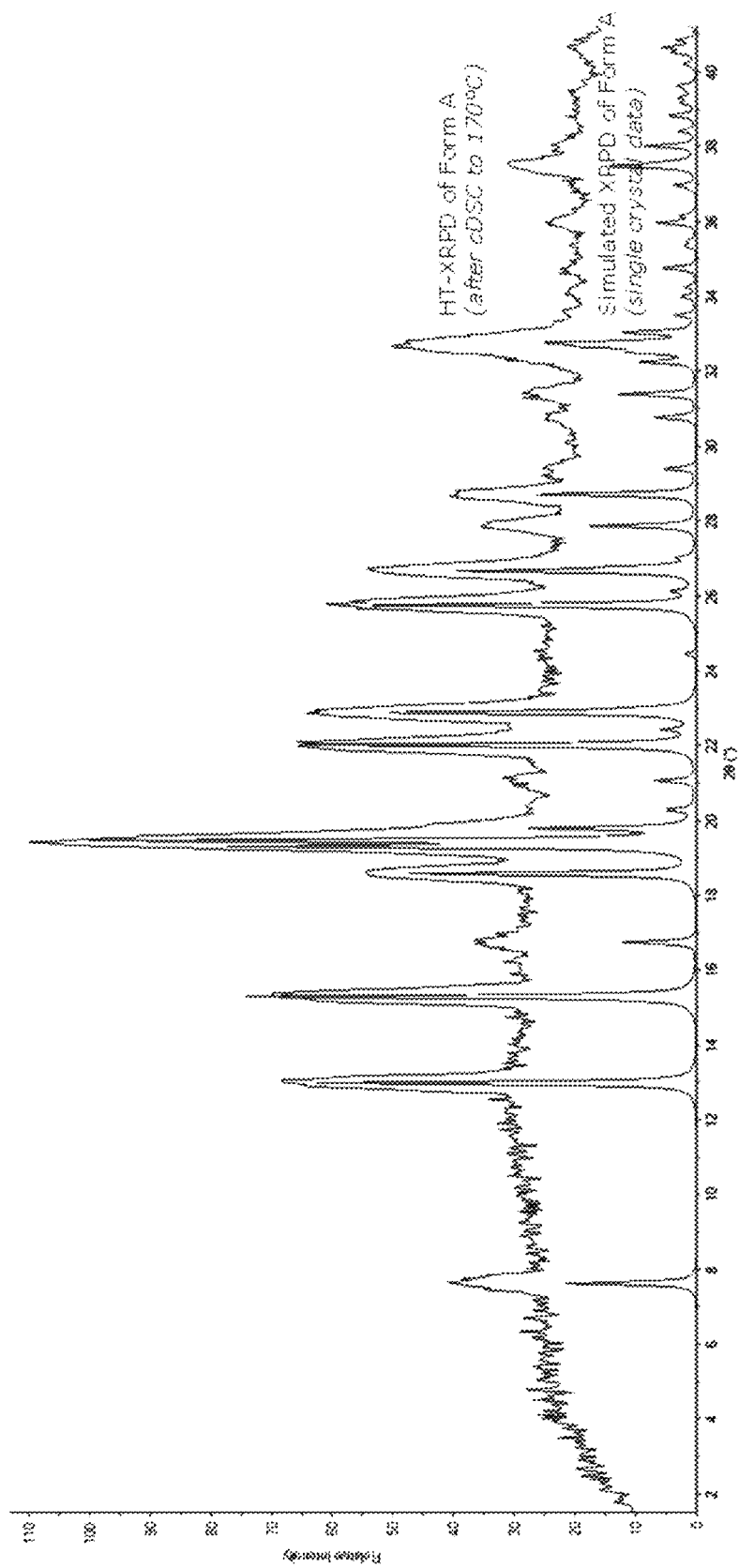
FIG. 5 shows representative simulated XRPD and HT-XRPD of aza-T-dCyd Form A following the second cycling DSC.
Figure 6:
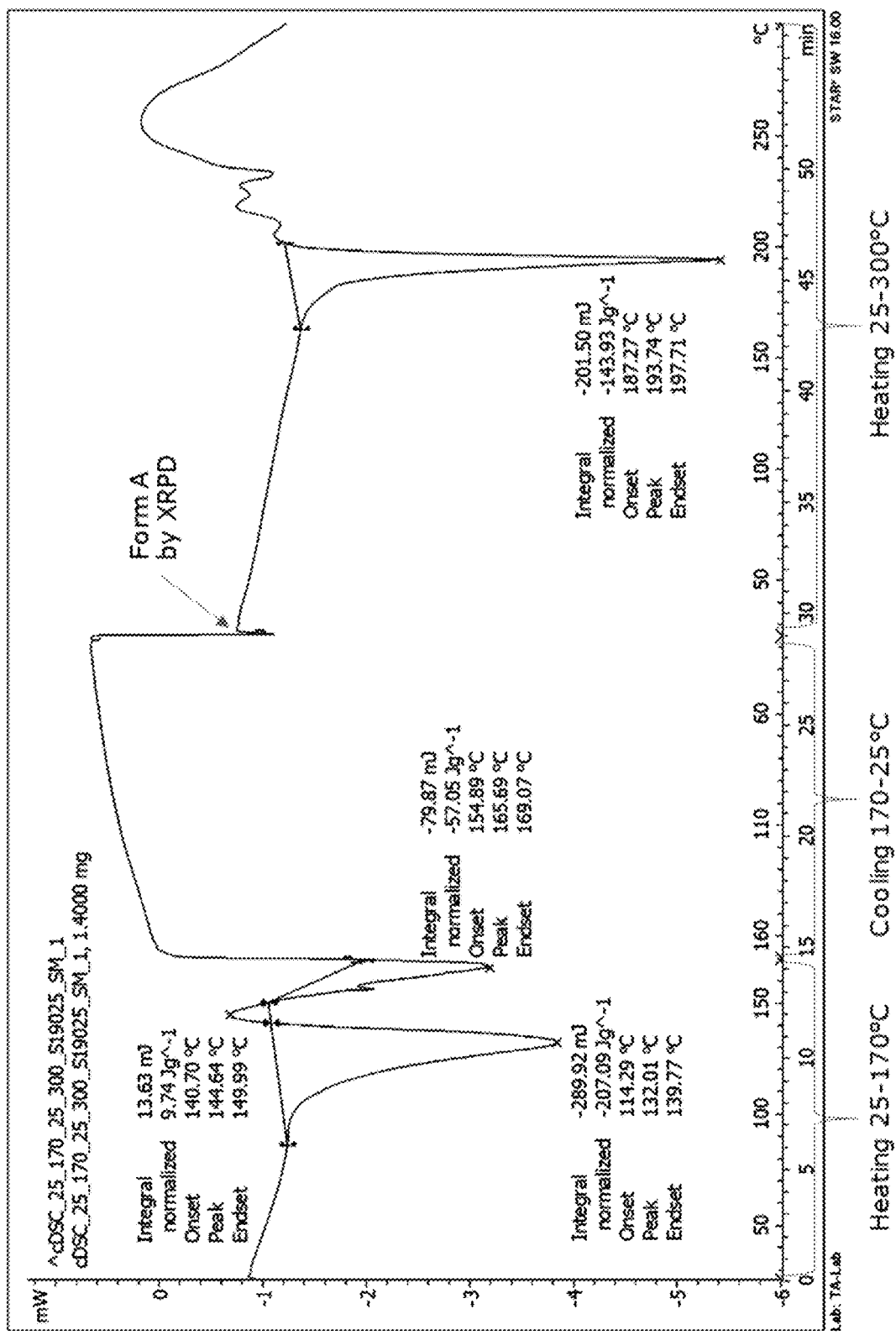
FIG. 6 reports the cycling DSC of aza-T-dCyd starting material (SM).

From XRPD and single crystal structure analysis it was found that the starting material consisted of a mixture of crystalline phases. To further investigate the nature of the thermal events, two cycling DSC experiments were performed on the starting material. One sample was heated to 170° C. and cooled back to RT. The obtained solid was analyzed by XRPD and matched the simulated pattern of Form A (FIG. 5). In the second cycling DSC experiment, the starting material was heated to 170° C., cooled to 25° C. and then heated to 300° C. (FIG. 6). During cooling no thermal events were observed, and in the second heating cycle only the endothermic melting event at 194° C. was observed, confirming the melting temperature of Form A.

Figures 7A, 7B:
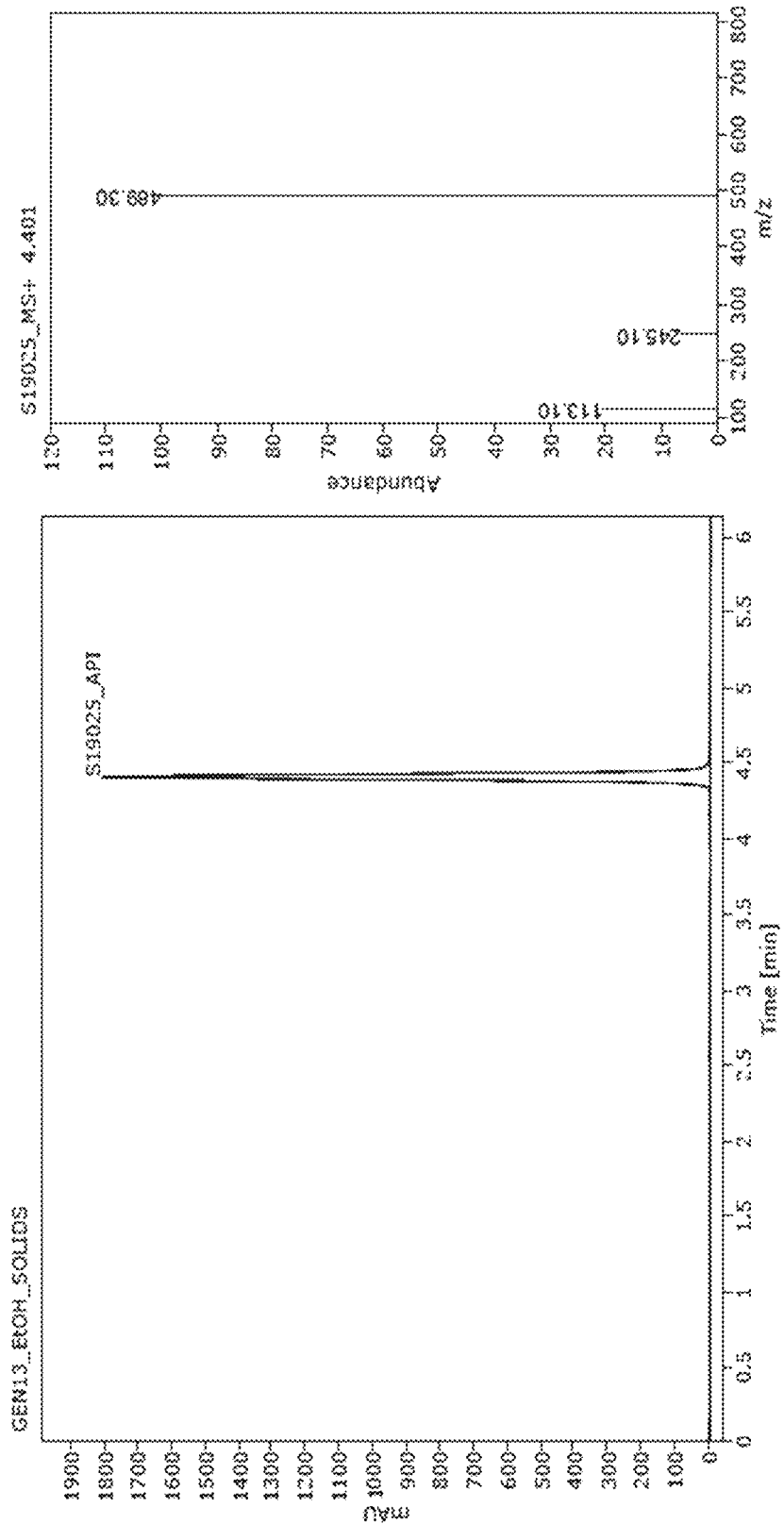
FIG. 7A and FIG. 7B show representative results of LCMS of aza-T-dCyd starting material (SM). Specifically.

The chemical purity of aza-T-dCyd was assessed by LCMS analysis. The analysis confirmed the chemical purity of 99.8% (area %) (FIG. 7A and FIG. 7B). The MS spectrum (positive scan mode) showed an ion with a m/z of 489.3, that could belong to the species [2M+H]$^+$ and a lower intensity ion at 245.1 m/z, that could belong to the species [M+H]$^+$, confirming the molecular mass of the API of 244.3 g/mol.

Figure 8A:
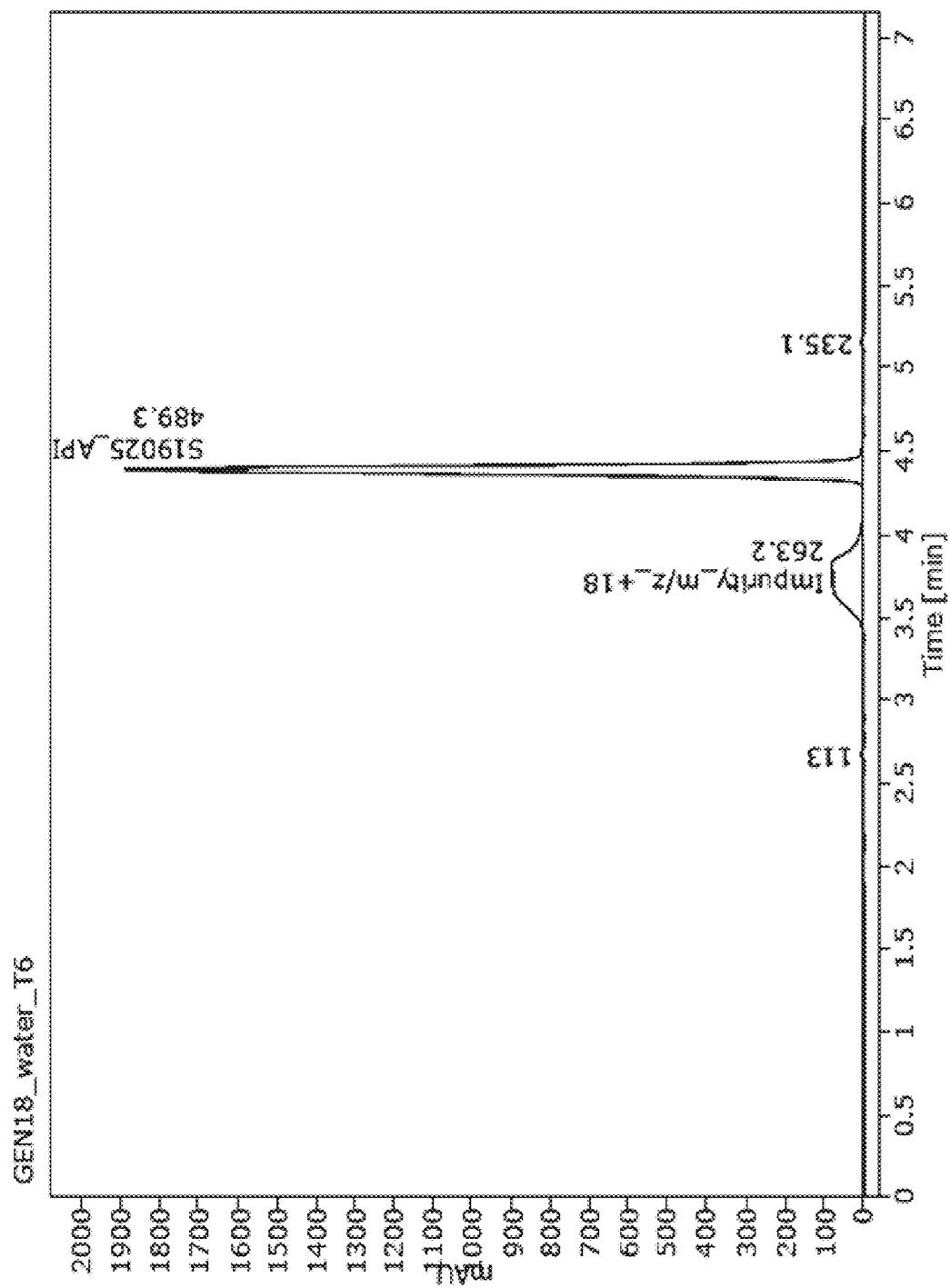
FIG. 8A-C show representative results of LCMS of aza-T-dCyd starting material (SM) following forming a solution in water. Specifically.
Figure 8C:
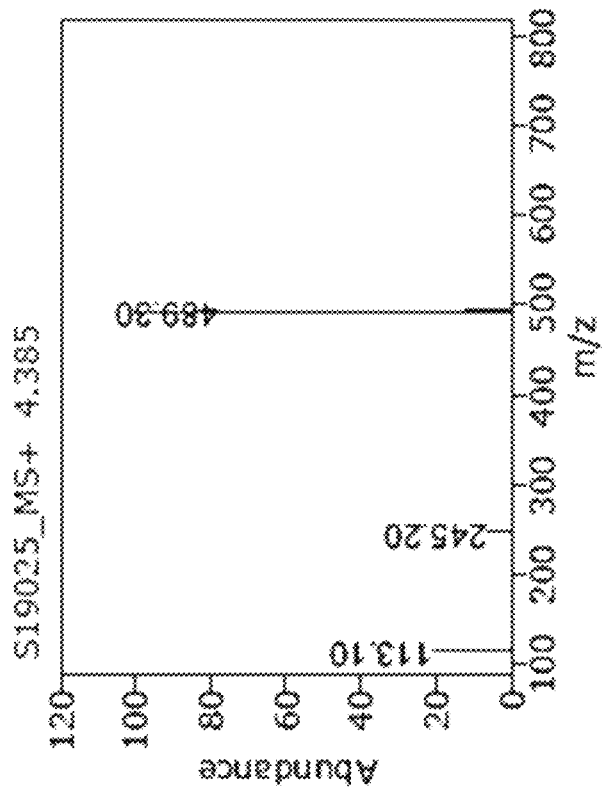
Figure 8B:
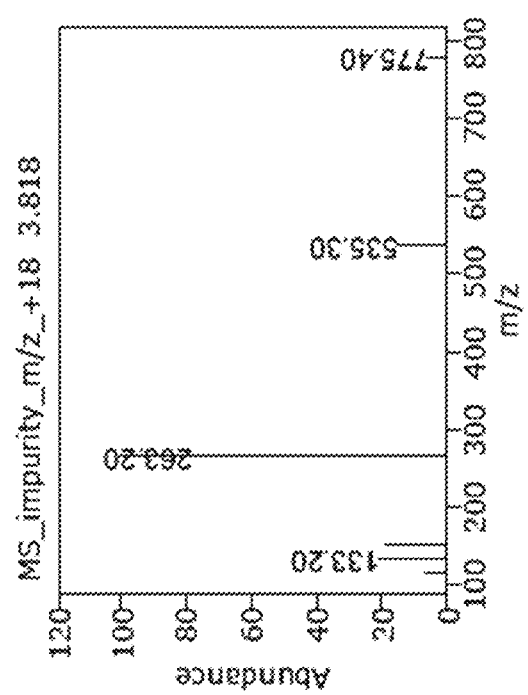

Aza-T-dCyd eluted from the column at 4.4 minutes and had an m/z of 489.3 [2M+H]$^+$ (FIG. 8A and FIG. 8B). During development of the LCMS method, an impurity appeared over time when the API was dissolved in aqueous media. The impurity that is formed was visible in the chromatograms at 3.8 min and had an m/z of 263.2 [M+18]$^+$ (FIG. 8A and FIG. 8C).

The chemical stability of aza-T-dCyd was determined. Aza-T-dCyd was prepared in 1,4-dioxane, acetonitrile (ACN), isopropanol (IPA), and methyl ethyl ketone. Each solution was divided over 3 vials and incubated at RT for 24 hours, at 50° C. for 1 hour, or at 80° C. for 1 hour. The solutions were analyzed by HPLC at the start and after the incubation time.

Figure 9:
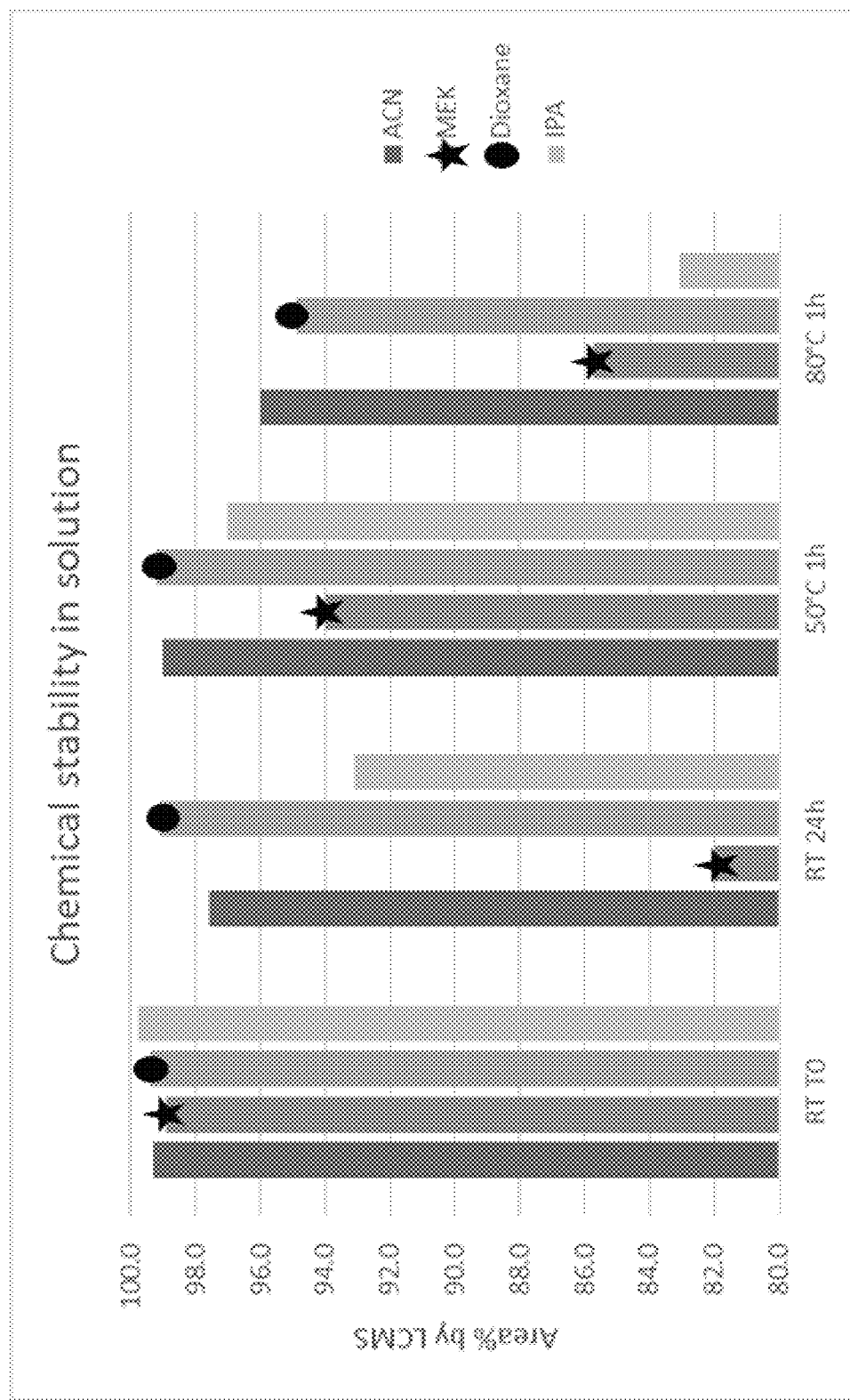
FIG. 9 shows representative data illustrating the chemical stability of aza-T-dCyd in various solutions.

The results are graphically presented in FIG. 9. At T0 the purity of the API was about 99% (area %) in each solvent. The compound remained stable (>95% purity) in acetonitrile and 1,4-dioxane at RT for 24 h, and at elevated temperatures for 1 hour. In IPA, the compound degraded significantly in the solution heated at 80° C. or when stored at RT for 24 h. In methyl ethyl ketone significant decomposition was observed after 1 hour at 50° C. and 80° C. and after 24 hour incubation at RT.

Additional stability tests were performed at 5° C. Suspensions of the starting material were prepared in water, acetonitrile, ethanol (EtOH), and isopropanol. The mother liquors of the suspensions and the water solution were analyzed by HPLC at regular intervals over 3 days.

Figure 10:
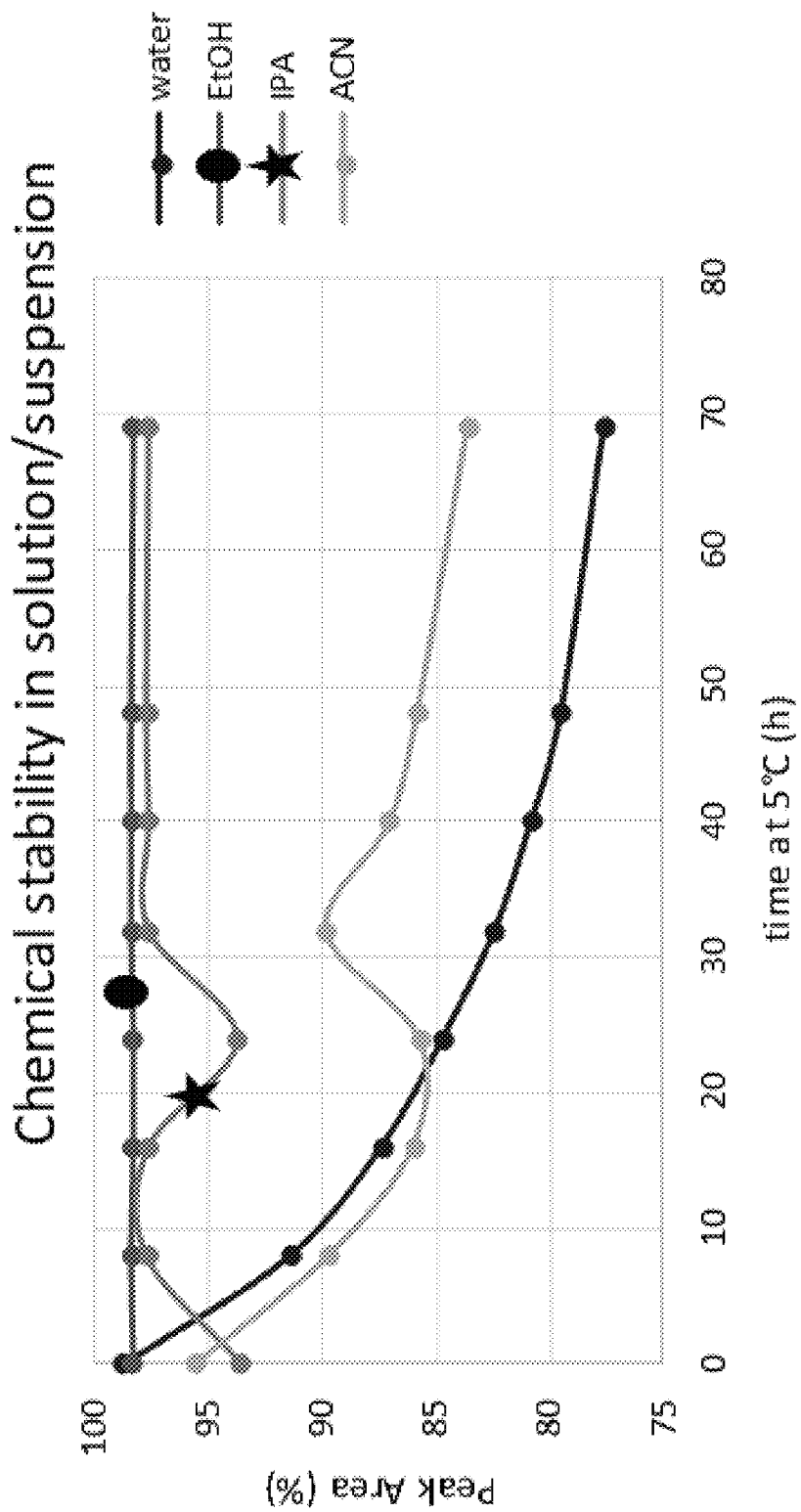
FIG. 10 shows representative data illustrating the chemical stability of aza-T-dCyd in various solutions over time.

The results are graphically presented in FIG. 10. The purity of the aza-T-dCyd is plotted in area % against time. The data points were obtained from single measurements from the same solution. The aza-T-dCyd in ethanol and IPA remained stable for 70 hours, whereas in acetonitrile and water the aza-T-dCyd purity decreased over time to 84% and 78%, respectively.

The solid phases from the suspensions were also evaluated for purity after 72 h. The solids recovered from the four solvents had a purity of about 99% (area %). See Table 2. Therefore, the aza-T-dCyd appeared chemically stable in the solid phase after 70-hour incubation at 5° C.

TABLE 2

| Solid Phase | Purity of Aza-T-dCYd after 72 h at 5° C. (area %) |
| --- | --- |
| Water | — |
| EtOH | 99.8 |
| IPA | 99.4 |
| ACN | 98.8 |

4. Example 2: Generation of Amorphous Material

Attempts to produce an amorphous material from starting material for a polymorph screen were made by freeze drying solutions of aza-T-dCyd. To obtain aza-T-dCyd solutions in organic solvents for freeze drying experiments, aza-T-dCyd was added to water, water/1,4-dioxane (50/50), water/THF (50/50) and water/tert-butyl alcohol (50/50% (v/v)). Freeze drying the aza-T-dCyd solutions led to poor crystalline materials that contained impurities.

5. Example 3: Solubility Studies

The thermodynamic solubility of aza-T-dCyd was determined according to the shake-flask method. Suspensions of the crystalline aza-T-dCyd were prepared in 25 neat solvents. Small aliquots of solvent were added to the aza-T-dCyd until thin suspensions were obtained. Subsequently, the samples were equilibrated at RT under continuous stirring for 24 hours. After equilibration, a small aliquot of mother liquor was filtered and analyzed by HPLC. The concentration of the solute was determined against a calibration curve of the aza-T-dCyd. The solubility values of aza-T-dCyd at room temperature are listed in Table 3 according to the US Pharmacopeia's classification (USP29). The aza-T-dCyd was soluble in high boiling point solvents such as DMF and DMA. Generally, aza-T-dCyd was slightly or very slightly soluble in polar solvents and practically insoluble in non-polar solvents.

TABLE 3

| Solvent | Solubility (mg/mL) | USP29 class. |
|---|---|---|
| Dimethylformamide | 65.8 | Soluble |
| N,N-dimethylacetamide | 60.0 | |
| 2,2,2,-trifluoroethanol | 4.1 | Slightly |
| Methanol | 3.6 | Soluble |
| Ethanol | 0.8 | Very |
| 1-propanol | 0.4 | Slightly |
| 2-propanol | 0.4 | Soluble |
| 1,4-dioxane | 0.3 | |
| 2-butanol | 0.3 | |
| Acetone | 0.2 | |
| 4-methyl-2-pentanone | 0.1 | |
| Tetrahydrofuran | 0.1 | |
| Acetonitrile | 0.1 | |
| 2-methyltetrahydrofuran | 0.1 | |
| 1,2-dimethoxyethane | 0.1 | |
| Anisole | <0.1 | Practically insoluble |
| Chloroform | <0.1 | |
| Cumene | <0.1 | |
| Cyclohexane | <0.1 | |
| Dichloromethane | <0.1 | |
| Diethyl ether | <0.1 | |
| Ethyl acetate | <0.1 | |
| Ethyl formate | <0.1 | |
| Isopropyl acetate | <0.1 | |
| Methyl ethyl ketone | <0.1 | |
| Heptane | <0.1 | |
| p-Xylene | <0.1 | |
| tert-butyl methyl ether | <0.1 | |
| Toluene | <0.1 | |

6. Example 4: Polymorph Screen

A polymorph screen was performed by combining 6 different crystallization techniques with a range of neat organic solvents and solvent mixtures. Considering the poor aza-T-dCyd thermal stability in solution and the limited stability of the aza-T-dCyd in water and ketones, the conditions for the screening experiments were selected such that: (1) experiments were initiated with the crystalline starting material; (2) the compound stayed in solution for a limited time (<5 days); (3) high temperatures were avoided (<50° C.); (4) the solid aza-T-dCyd was handled in a glovebox under dry conditions (relative humidity about 200%) as much as possible to avoid uptake of moisture; (5) water was avoided, and the use of ketones was limited; and (6) gentle stress conditions to evaluate the physical stability of the obtained solids.

The following crystallization techniques were applied:

Solvent equilibration experiments. Solvent equilibration experiments were performed at two temperatures: RT for 1 day and 5° C. for 5 days. Suspensions of aza-T-dCyd were prepared with the crystalline starting material in different solvents and upon completion of the equilibration time, the solids were separated from the mother liquors.

Evaporative crystallization experiments. Evaporative crystallization experiments were set up using the filtered mother liquors recovered from the solvent equilibration experiments performed at RT and from solvent mixtures. The solvents were slowly evaporated at ambient conditions, followed by further drying under vacuum (10 mbar) at 50° C.

Anti-solvent experiments. Anti-solvent experiments were performed using a combination of 10 solvents and anti-solvents by reverse addition: a small volume of a highly concentrated solution of aza-T-dCyd was added to 20 mL of anti-solvent (one step).

Thermocycling experiments. Thermocycling experiments were performed by preparing aza-T-dCyd suspensions in different solvents and solvent mixtures at RT. The resulting suspensions were subjected to a temperature profile, between 5 and 50° C.

Sonication experiments. Sonication experiments were performed by sonicating the crystalline starting material in the presence of a small amount of solvent.

Vapor diffusion into solution experiments. Vapor diffusion into solution experiments were performed as a slow method of anti-solvent crystallization. A saturated aza-T-dCyd solution was exposed to vapors of an anti-solvent for one week at RT.

All obtained solids were analyzed by HT-XRPD after drying overnight in a glovebox at RT and 20% relative humidity and after drying overnight under vacuum (10 mbar) at RT. If mother liquors were recovered, mother liquors (ML) were evaporated and recovered solids were analyzed by HT-XRPD. Subsequently, all solids were exposed to accelerated aging conditions (25° C./60% RH) for two days and then re-analyzed by HT-XRPD.

Form A was the most abundant crystalline phase recovered from the screening experiments. This form was found from all crystallization methods and in a broad variety of solvents and solvent mixtures. From the solvent equilibration experiments, it was observed that Form A was obtained as a pure phase from solvents in which the aza-T-dCyd was slightly soluble or very slightly soluble.

In some solids, besides the XRPD pattern of Form A, the presence of peaks already observed in the received starting material were detected and described above. The received batch of aza-T-dCyd contained 70% of Form A and 30% of other crystalline phases. The presence of 30% of other phases was most clearly highlighted by peaks appearing in the XRPD patterns at 16.0°, 17.6°, 24.8°, 26.3° and 34.1° 2θ. By evaluation of the solids recovered from the polymorph screen experiments, the assignment and classification of such impurity peaks was attempted. An overview of the XRPD patterns of the starting materials, Form A, Form B, Forms A+C1, Forms A+C2, Forms A+D1, and Forms A+D2 are shown in FIG. 11.

The peak at 26.3° 2θ belonged to Form B. The peak observed at 16.0° 2θ represents Form C1 and peaks at 16.0 and 17.6° 2θ were attributed to Form C2. The peak observed at 24.8° 2θ was attributed to Form D1 and the peaks at 24.8 and 34.1° 2θ were attributed to Form D2. Based on this assignment, some solids were classified as Forms A+D1/D2, A+C1/C2 or A+B+D2.

Form B was obtained as a pure phase by solvent equilibration in DMA and DMF, both at RT and at 5° C., and also from the thermocycling experiment in DMSO/2-ethyl-1- hexanol (50/50). Form B was physically unstable and converted to Form A after storage at 25° C., 60% relative humidity.

The classes C and D were never observed as pure crystalline phases but always in mixture with Form A. In most cases, these mixtures converted to Form A after storage at 25° C., 60% relative humidity.

Novel forms were found from the solution-based crystallization methods, where no seeds of Form A were present. These novel forms were classified as Forms E, F, G1, G2, H, I, J, K. Form E was obtained from anti-solvent addition in DMA/chloroform or evaporative crystallization from DMA/TBME (80/20). Form E converts to Form A after storage at 25° C., 60% relative humidity.

Form F was obtained from vapor diffusion or evaporative crystallization in various solvents. Form F was physically stable. The peaks of Form F are 6.06°, 12.10°, 13.02°, 14.38°, 15.94°, 17.50°, 19.62°, 21.18°, 22.34°, 26.18°, 27.42°, 28.50°, 29.90°, 32.66°, 35.02°, 36.30°, 38.94°, and 41.06° 2θ.

Forms G1 and G2 have similar XRPD patterns, where some peaks are shifted between the two forms. Form G1 was obtained from anti-solvent addition or sonication. Form G2 was obtained from evaporative crystallization with DMA/EtOH. Both Form G1 and Form G2 convert to Form A after storage at 25° C., 60% relative humidity.

Form H was obtained from evaporative crystallization in several solvent mixtures. This form is unstable. When obtained from NMP, Form H converted to Form F. When obtained from other solvents, Form H converted to Form A.

Form I was obtained from evaporative crystallization from DMSO/IPA. Form I converts to Form A after storage at 25° C., 60% relative humidity.

Form J was obtained from vapor diffusion into solution with DMF as the solvent and THF as an antisolvent. Form J converts to Form A after storage at 25° C., 60% relative humidity.

Form K was observed in a mixture with Form F following evaporative crystallization from DMF. Form K converted to Form F after storage at 25° C., 60% relative humidity.

Form L was observed in solids following storage at 25° C. and 65% relative humidity.

The XRPD patterns for each of these novel forms is shown in FIG. 12.

7. Example 5: Characterization of Novel Forms of Aza-T-dCyd

Each unique form identified in the screen was further characterized by TGMS and LCMS. Forms A and F appeared to be anhydrous, whereas the other forms were solvated. Table 4 summarizes crystallization conditions for the described forms of aza-T-dCyd (AAC indicates storage at 25° C., 60% relative humidity). Table 5 summarizes the properties of various aza-T-dCyd forms (AAC indicates storage at 25° C., 60% relative humidity).

TABLE 4

| Form | AAC | Obtained from Crystallization | |
|---|---|---|---|
| | | Method | Solvent |
| A | A | All | Various |
| B | A | SLP (RT, 5° C.) | DMA, DMF |
| | | TCP | DMSO/2-ethyl-1-hexanol |
| A + C1 | A | SLP (RT) | Various |
| A + C2 | A or A + C2 | SLP (RT), VDL | Various |
| A + D1 | A | SLP (RT, 5° C.) | Various |
| A + D2 | A | SLP (RT, 5° C.) | Various |
| | | TCP | Various |
| | | Sonication | Various |
| | | VDL | HFIP/Chloroform |
| | | AS (dry solid) | HFIP/Heptane |
| A + D2 | A + L | ECP | MeOH |
| A + B + D2 | L | ECP | TFE |
| E | A | AS | DMA/Chloroform |
| | | ECP | DMA |
| | A + F | ECP | DMA/TBME (80/20, v/v) |
| F | F | VDL | HFIP/MEK |
| | | VDL | DMF/Chloroform |
| | | VDL (ML) | MeOH/DCM |
| | | VDL (ML) | TFE/Pentane |
| | | ECP | DMF/ACN (80/20, v/v) |
| | | ECP (ML) | DMF/EtOAc (50/50, v/v) |
| G1 | A | AS | NMP/Cyclohexane |
| | | AS | NMP/2-MethylTHF |
| | | Sonication | NMP |
| | | TCP | NMP/2-Methoxyethanol (50/50, v/v) |
| | | VDL (ML) | NMP/EtOAc |
| G2 | A | ECP | DMA/EtOH (80/20, v/v) |
| H | F + H | ECP | NMP/THF (80/20, v/v) |
| | | ECP | NMP/IPA (80/20, v/v) |
| | A | VDL (ML) | DMF/THF |
| | | VDL (ML) | DMSO/DCM |
| I | A | ECP | DMSO/IPA (80/20, v/v) |
| J | A | VDL | DMF/THF |
| F + K | F | ECP | DMF |

TABLE 5

| Form | AAC | Mass loss, % (temp range, ° C.) | Solvent | Nature | Decomposition (° C.) |
|---|---|---|---|---|---|
| A | A | 0.7 (30-190) | Residual solvent | Anhydrate | 200 |
| B | A | 25.0 (30-170) | DMA (0.93 eq.) | Non-stoichiometric solvate | Gradual on heating |
| A + C2 | A + C2 | 0.7 (30-160) | Inconclusive | Inconclusive | 190 |
| A + D2 | A | 5.1 (90-170) | Inconclusive | Solvated | 195 |
| E | A | 25.8 (90-160) | DMA (0.98 eq.) | Mono-DMA solvate | 200 |
| F | F | 1.1 (30-140) | Residual solvent | Anhydrate | 170 |
| G1 | A | 27.5 (90-160) | NMP (0.93 eq.) | Mono-NMP solvate | 200 |
| G2 | A | 14.6 (70-120) | DMA (0.48 eq.) | Hemi-DMA solvate | 190 |
| H | F + H or A | 15.3 (30-180) | NMP (0.45 eq.) | Non-stoichiometric solvate | 180 |
| I | A | 14.7 (30-170) | DMSO (0.54 eq.) | Hemi-DMSO solvate | 190 |
| J | A | 7.6 (120-170) | THF (0.28 eq.) | Non-stoichiometric solvate | 200 |
| F + K | F | 6.3 (30-160) | DMF (0.22 eq.) | Solvated | 195 |
| A + B + D2 | L | 2.8 (30-170) | Water (0.39 eq.) | Inconclusive | 170 |

Form A obtained from the solvent equilibration experiment at RT in TFE was used for the analytical characterization. The TGMS result showed the release of about 0.7% of residual solvent in the temperature range 30-190° C. (FIG. 12A). An endothermic event was observed in the DSC trace at 205° C., due to melting and decomposition (FIG. 12B). The LCMS analysis confirmed the Form A's integrity with a purity of 100% (area %) (FIG. 12C).

Figure 15A:
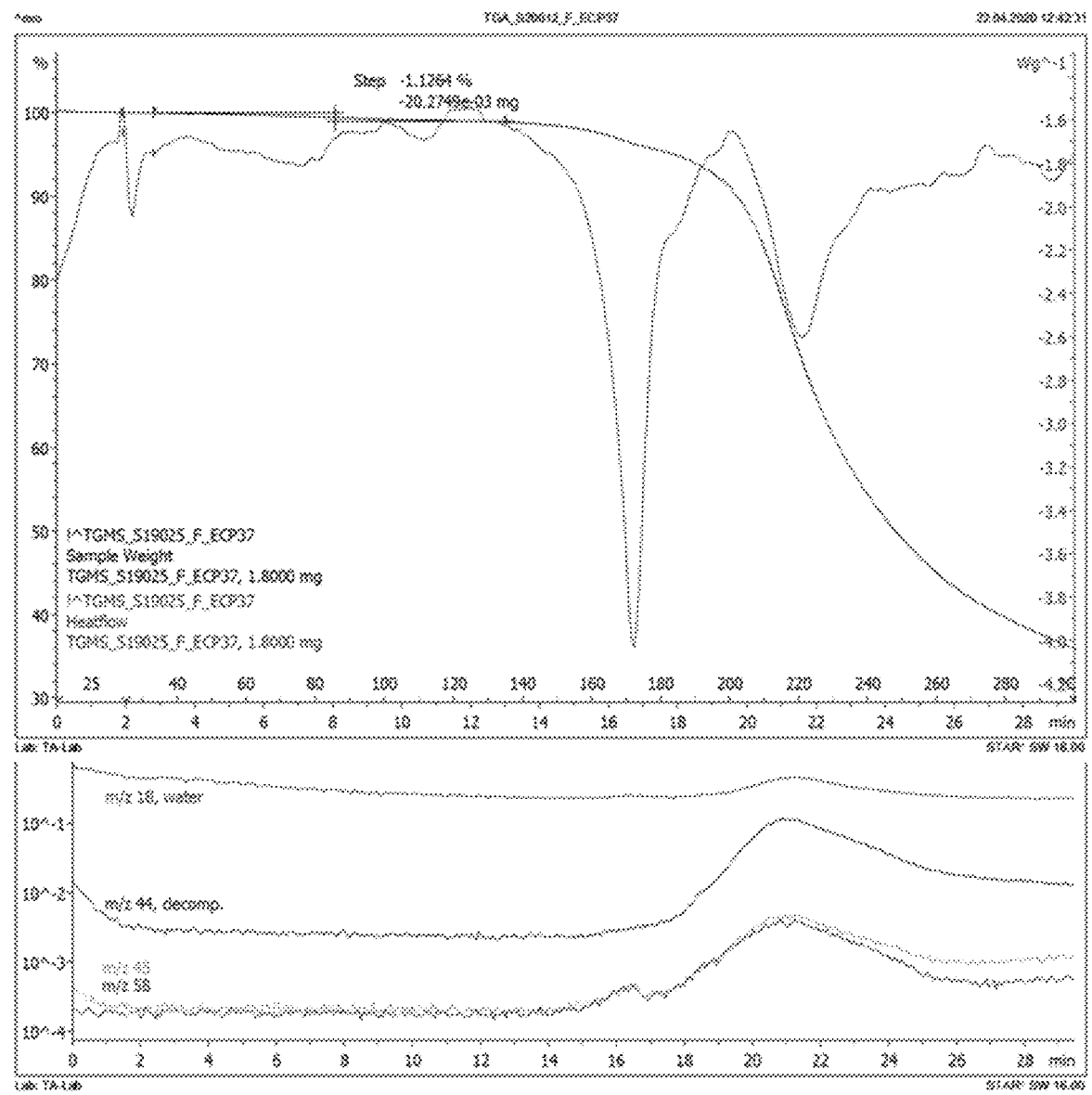
FIG. 15A-C show representative chemical analyses of Form F. Specifically.
Figure 15B:
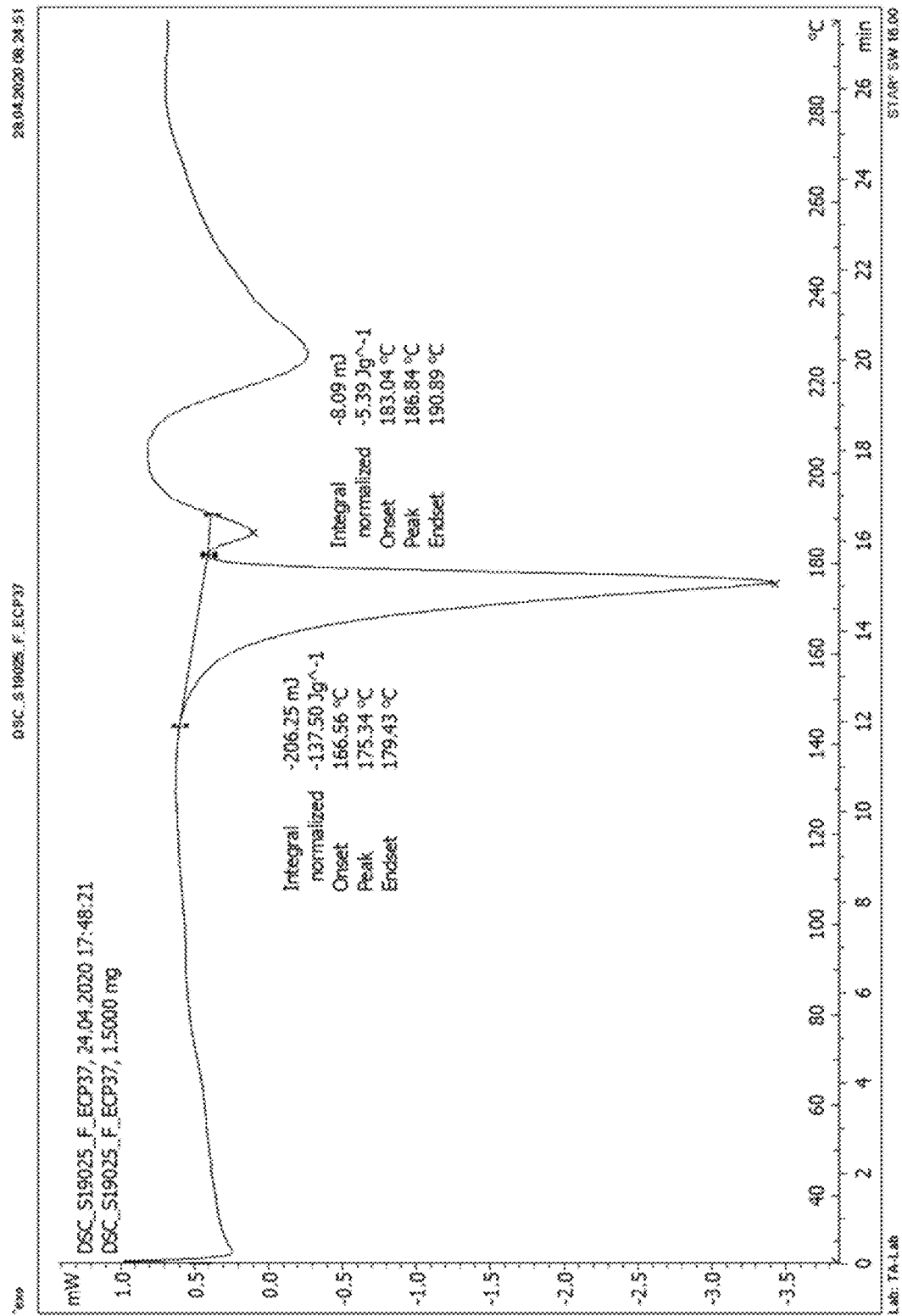
Figure 15C:
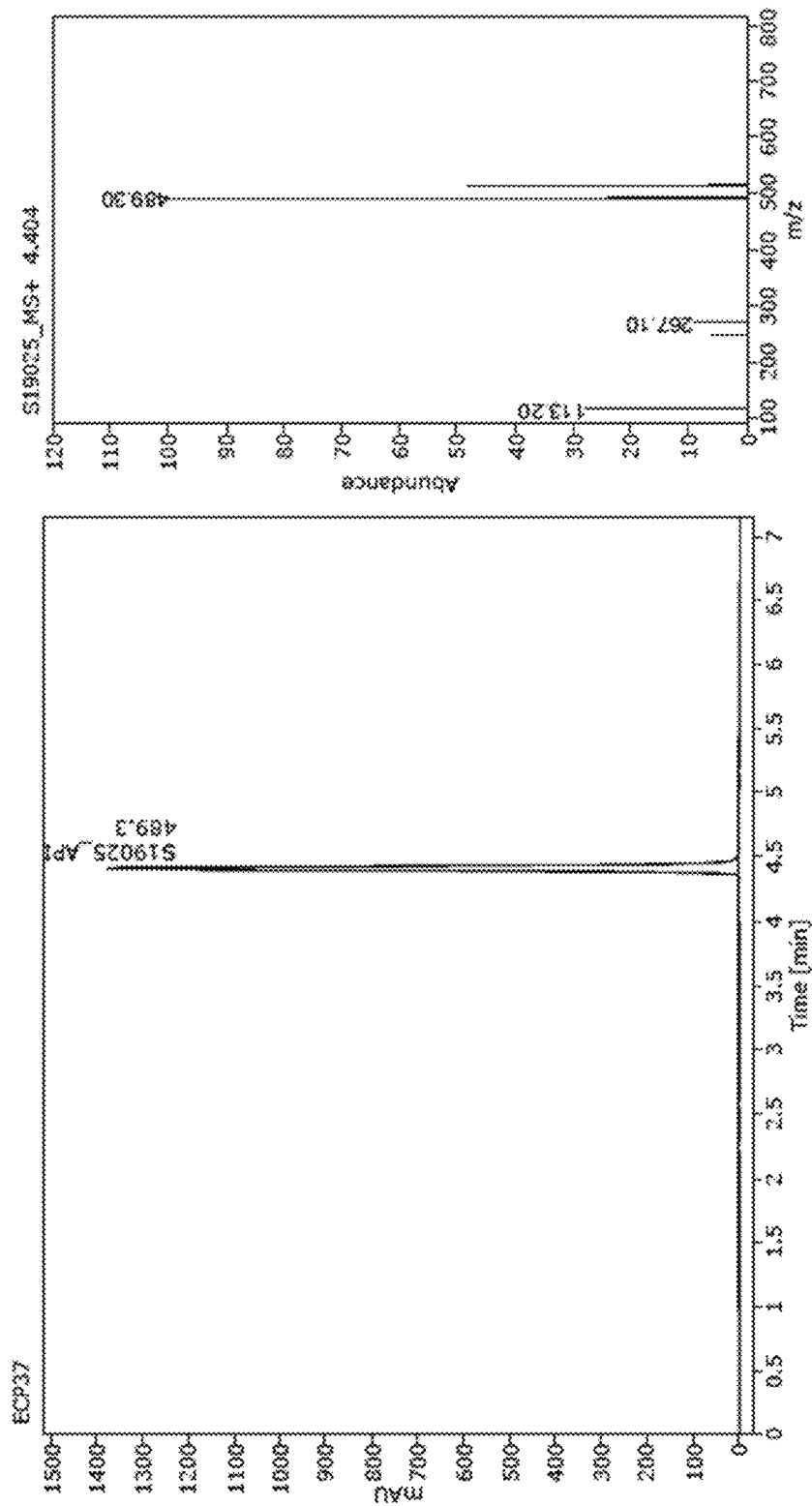

Form F obtained from the evaporative crystallization experiment using DMF/acetonitrile (80/20, v/v) was used for characterization. The TGMS result showed a small loss of 1.1% between 30 and 140° C., most likely due to residual solvent (FIG. 15A). The DSC trace showed one endothermic event around 170° C., due to melting and decomposition (FIG. 15B). The LCMS analysis confirmed the API's integrity with a purity of 100% (area %) (FIG. 15C).

Form A had a higher melting temperature than Form F and can be considered as the thermodynamically more stable form. Both Form A and Form F are anhydrous.

Forms B, C2, D2, E, G1, G2, H, I, J, and K are each solvated and convert to Form A when stored at 25° C., 60% relative humidity for two days.

Form B obtained from the solvent equilibration experiment in DMA at RT was further characterized. The TGMS result showed a gradual mass loss upon heating with a mass loss of 25.0% between 30 and 170° C. Due to the gradual mass loss upon heating, it is unclear at which temperature the decomposition starts. Form B might be a non-stoichiometric solvate which can be formed with different solvents. The LCMS analysis showed a purity of the solid of 97.3% aza-T-dCyd and the presence of an impurity of 2.7% (area %).

Form C2 represented two additional peaks that were observed in the XRPD pattern in mixtures with other forms. The TGMS analysis showed a mass loss of 0.7% in the temperature range 30-160° C. The heat flow signal showed only one endothermic event around 190° C., which could be related to the melting and decomposition of Form A. Since in the mixture with Form A, Form C2 was only present in traces, the investigations about Form C2 are inconclusive and therefore the nature of this form remains unclear. However, it seems to be a true (pseudo-)polymorph of aza-T-dCyd since the chemical purity of the overall solid sample was 100% (area %).

Form D2 represented two additional peaks that were observed in the XRPD pattern in mixtures with Form A. The TGMS analysis of Forms A+D2 showed that Form D2 is most likely a solvated form. A mass loss of 5.1% was observed between 90 and 170° C. The result was inconclusive about the solvent that was released. The LCMS analysis on the mixture of the forms confirmed the aza-T-dCyd's integrity with a chemical purity of 100% (area %).

Form E obtained from the evaporative crystallization experiment with DMA was further analyzed by TGMS and LCMS. The TGMS result showed a mass loss of 25.8% of DMA, which corresponds to 1 molar equivalent of solvent. The solvent was released in a stepwise manner between 90 and 160° C., suggesting that Form E is a mono-DMA solvate. After the desolvation an endothermic event was recorded at 200° C., most likely corresponding to the melting of Form A. The compounds integrity was confirmed by the LCMS analysis.

Class G is an isostructural class of solvates. Forms G1 and G2 were further characterized by TGMS and LCMS. The LCMS analysis confirmed the compounds integrity (area % of 100%). Form G1 obtained from the anti-solvent addition experiment using NMP and cyclohexane was used for the characterization. The TGMS result showed a mass loss of 27.5% between 90 and 160° C. in a stepwise manner. The 27.5% mass loss corresponds to about 1 molecule of NMP per aza-T-dCyd molecule, and therefore Form G1 could be a mono-NMP solvate. The DSC signal recorded two endothermic events around 110 and 150° C. due to solvent loss, and a third endothermic event at 200° C., that could correspond to the melting of Form A. Form G2 was obtained by evaporative crystallization from DMA/ethanol 80/20 (v/v). The mass loss of 14.6% observed by TGMS between 70 and 120° C. corresponded to 0.5 molar equivalents of DMA. This suggested that Form G2 could be a hemi-DMA solvate. In the DSC signal two endothermic events were observed around 80 and 90° C., due to the solvent loss and a third endothermic event was observed around 195° C., due to melting and decomposition.

Form H obtained from evaporative crystallization from NMP/THF (80/20, v/v) was used for the characterization of Form H. The gradual mass loss observed by TGMS analysis was 15.3% between 30 and 180° C. corresponding to about 0.5 molar equivalent of NMP. Simultaneously, a broad endothermic event was observed around 130° C. Form H was observed in experiments using different solvents and therefore is most likely a non-stoichiometric solvate that can incorporate different solvent molecules in its crystal structure. Around 220° C. a second broad endothermic event was observed in the DSC trace, due to decomposition. From the TGMS data it was unclear where the solvent loss ended and thermal decomposition started; the events might be partly overlapping. To obtain a dry sample, the solids had to be dried under vacuum at 50° C. for 24 hours. This may have impacted the purity, as the LCMS data indicated that the solid had a purity of 82% (area %).

Form I was obtained by evaporative crystallization from DMSO/IPA (80/20, v/v). The TGMS data showed a gradual mass loss of 14.7% between 30 and 170° C. The mass loss of 14.7% corresponds to about 0.5 molar equivalents of DMSO. Form I could be a hemi-DMSO solvate. The DSC trace showed two broad endothermic events at 70° C. and 110° C., due to the mass loss and a third endothermic event around 190° C., due to melting and decomposition processes.

Form J precipitated by vapor diffusion into solution using DMF and THF and was further characterized. The TGMS data showed a mass loss of 7.6% of THF in a stepwise manner between 120 and 170° C. The mass loss corresponds to about 0.3 molar equivalents of THF and Form J is therefore most likely a non-stoichiometric solvate. The DSC trace recorded two endothermic events at 120 and 150° C. due to the solvent loss, and a third endothermic event was recorded at 200° C., matching the melting/decomposition event of Form A.

Form K was observed once in a mixture with Form F and was obtained by evaporation from a DMF solution. The mixture was further characterized. The TGMS analysis showed a mass loss of 6.3% between 30 and 160° C., possibly due to loss of DMF. The mass loss was accompanied by a small endothermic event around 110° C. Two large endothermic events were observed at 180 and 195° C. The endotherm at 195° C. could be due to the melting and decomposition of Form A. Because Form K was in a mixture with Form F (non-solvated form), Form K is most likely a solvated form.

Form L was a poor crystalline solid observed only after storage at 25° C., 60% relative humidity and in very low yield. In the TGMS analysis a mass loss of 2.8% was observed between 30 and 170° C., followed by decomposition. The lack of thermal events in the DSC trace could be due to the small amount of sample used for the analysis. It is uncertain if the mass loss is due to solvent trapped in the crystal structure or if it is residual solvent. No further characterization could be performed and hence the nature of Form L remains unclear.

The crystals obtained from the attempts to grow single crystals from an aza-T-dCyd solution in acetonitrile appeared to be an acetonitrile solvate. This phase was not observed in any of the screening experiments. The solvate crystallized in a monoclinic P2$_1$ space group, with cell unit dimensions of a=9.2948(15), b=7.3509(9), c=10.2312(15) Å, β=107.661(2)°, V=666.10(17) Å$^3$, Z=2 and a density of 1.423 g/cm$^3$. Because only single crystals were formed (very low yield), no further characterization was performed on this form and also the physical stability remains to be investigated.

8. Example 6: Pharmacokinetic Characteristics of Aza-T-dCyd

The pharmacokinetic characteristics of aza-T-dCyd (starting material; SM; aza-T-dCyd that has not yet been subjected to specific crystallization conditions) were studied as follows.

Aza-T-dCyd starting material (SM) was administered to six female NOD-SCID mice splitting into four groups. Group 1 was a vehicle control group. In group 2, 2.0 mg/kg of aza-T-dCyd starting material (SM) was administered once a day, and in group 3, 1.0 mg/kg of aza-T-dCyd starting material (SM) was administered twice a day. In groups 2 and 3, aza-T-dCyd starting material (SM) in the above amounts was administered for 5 days followed by 2 days as a rest period, and was administered again for another 5 days followed by 9 days as another rest period. This cycle was repeated. In group 4, 1.0 mg/kg of aza-T-dCyd starting material (SM) was administered once a day for five days followed by 2 days as a rest period, and this cycle was repeated. The tumor size in the mice was measured using a fluorescent agent, and the results were obtained as shown in FIG. 17.

Figure 17:
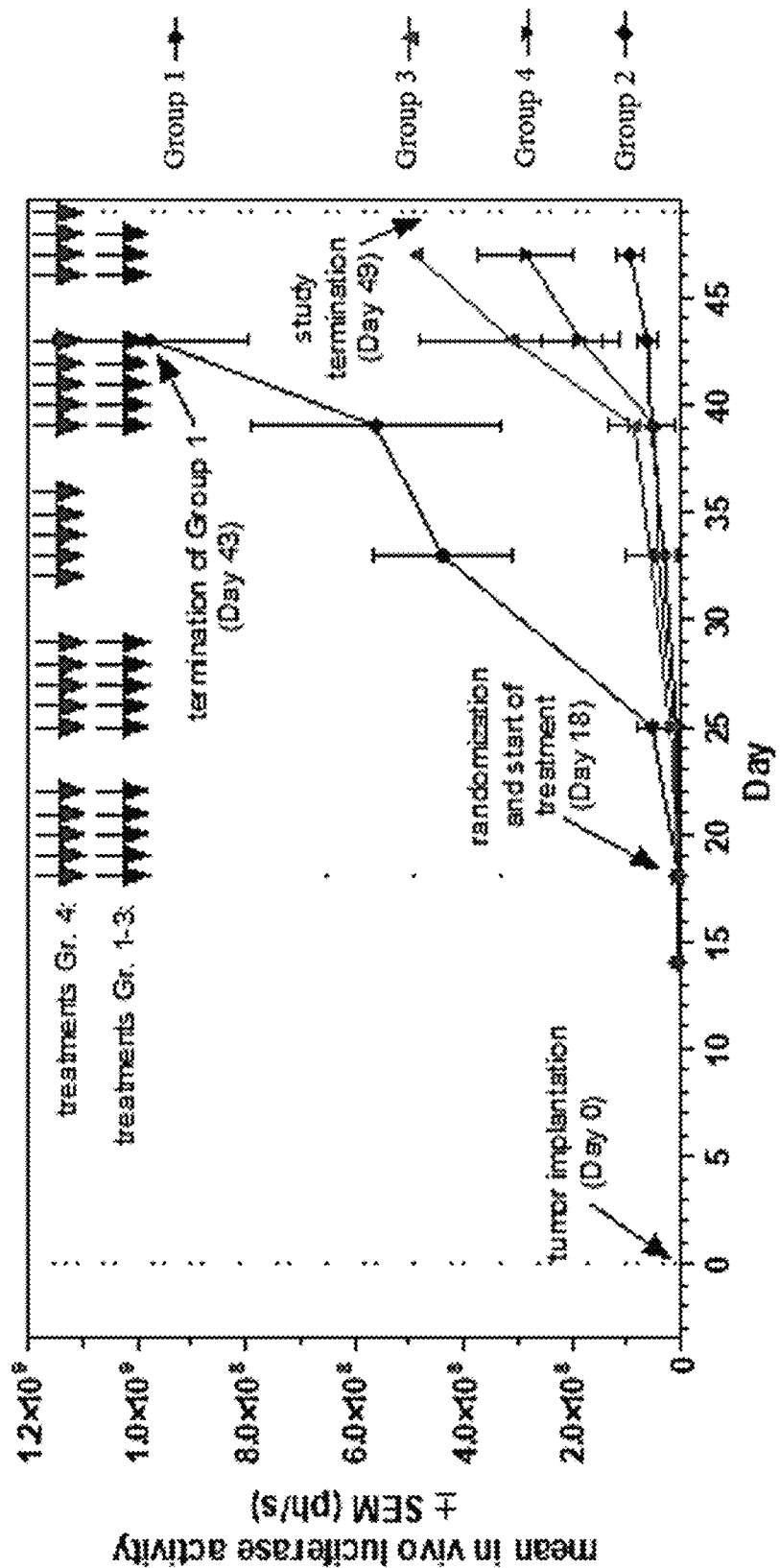
FIGS. 17 and 18 show in vivo luciferase activity data representing tumor sizes when aza-T-dCyd starting material (SM) was administered to female NOD-SCID mice.

As shown in FIG. 17, the tumor size was increased in Group 1 (the vehicle control group. In addition, it was confirmed that the increase of the tumor size was most greatly suppressed in Group 2. In contrast, although it was expected that the AUC of SM in Group 3 would be the same as that of Group 2, it was observed that the tumor size was sharply increased after 40 days of the administration. From the above, it was found that aza-T-dCyd is Cmax dependent rather than AUC dependent.

Figure 18:
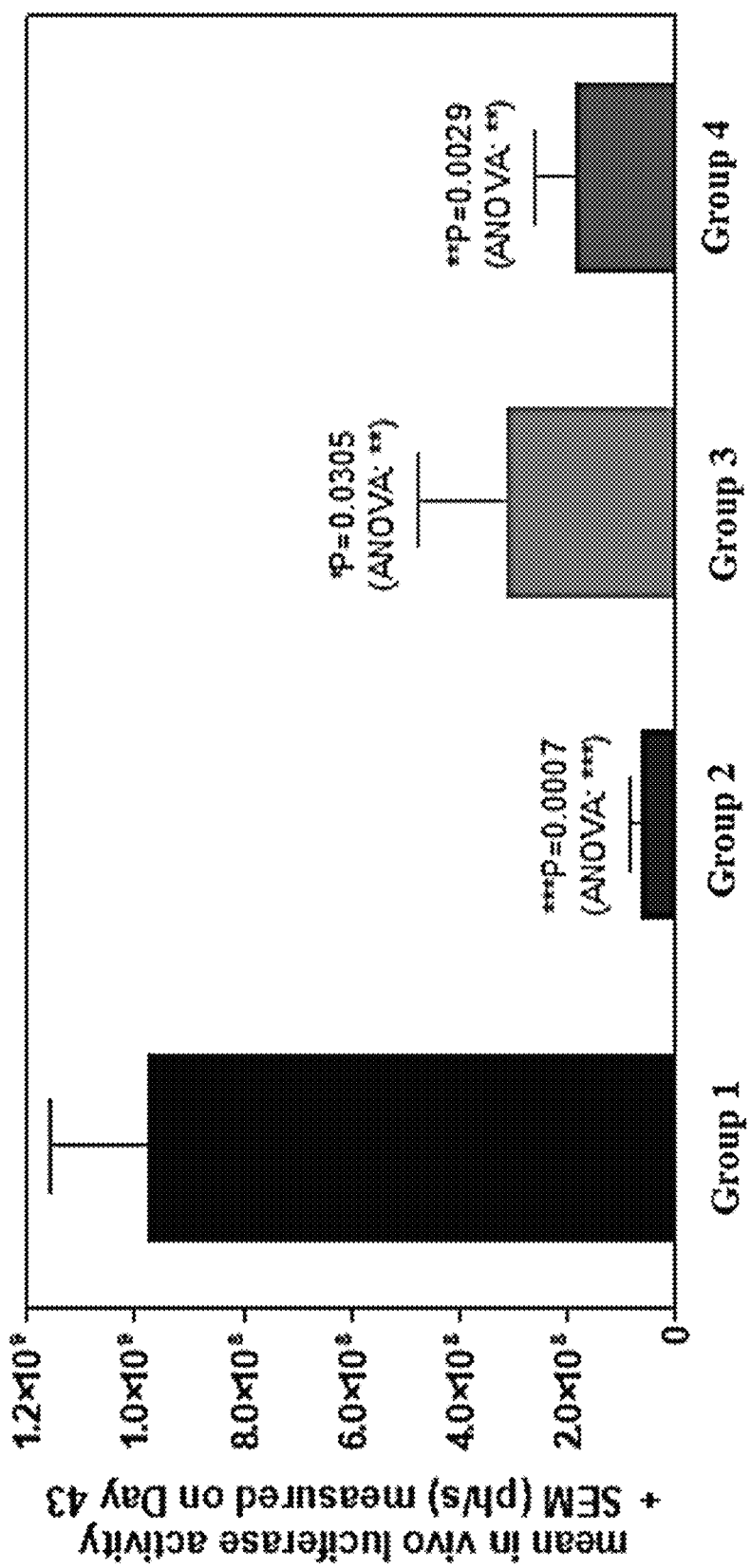

In addition, as shown in FIG. 18 demonstrating the results on day 43, the tumor size in Group 2 (2.0 mg/kg, once a day) was significantly smaller than Group 1 (1.0 mg/kg, twice a day).

Figure 19:
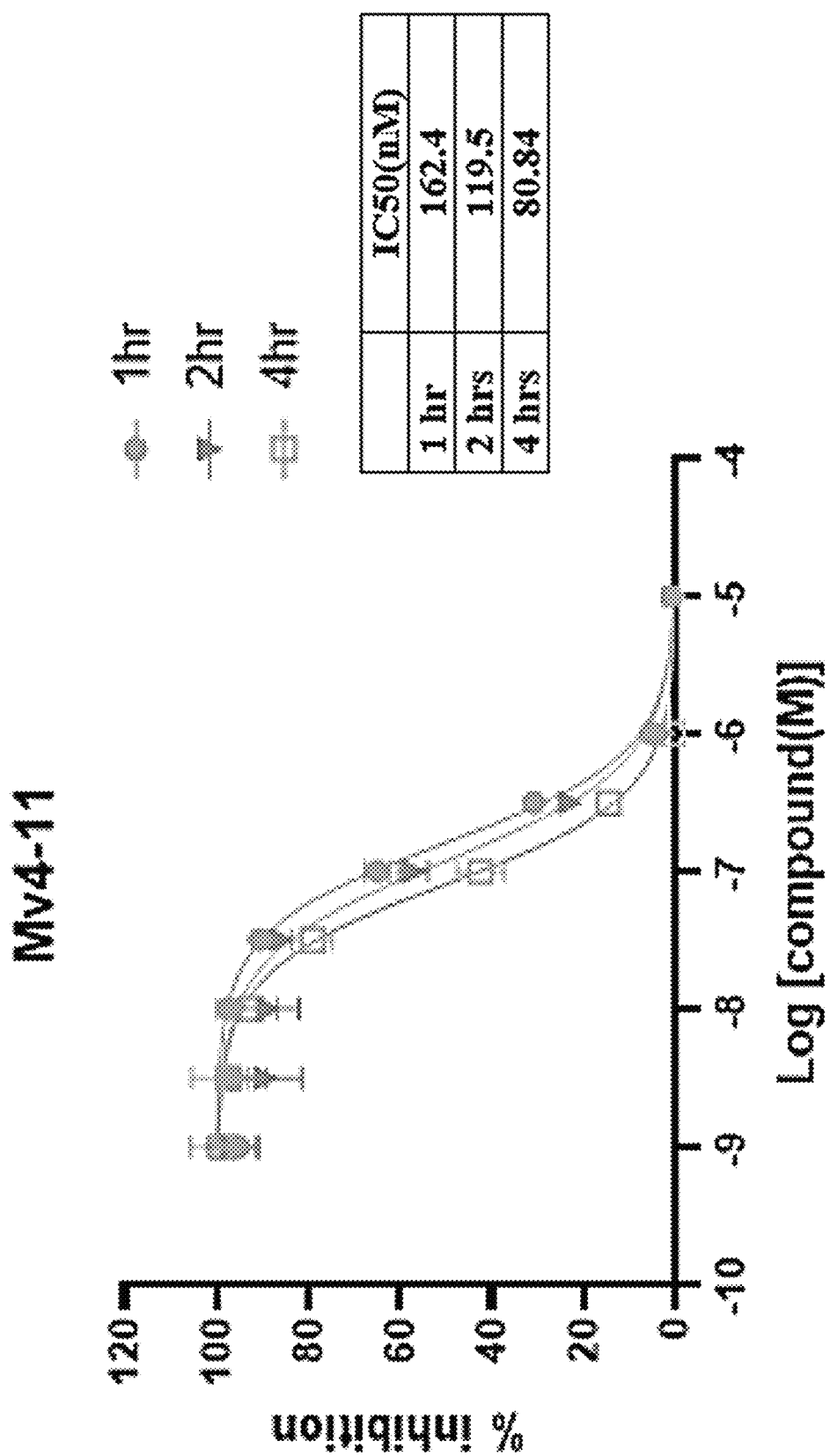
FIG. 19 shows half maximal inhibitory concentrations ($IC_{50}$) when blood cancer cells (Mv4-11) were treated with aza-T-dCyd starting material (SM).

Furthermore, the half maximal inhibitory concentration (IC$_{50}$) was measured at 1 hr, 2 hr, and 4 hr after the blood cancer cells (Mv4-11) were treated with aza-T-dCyd starting material (SM). The results are shown in FIG. 19. The measured IC$_{50}$ at 1 hr was about 160 nM, and thus the IC$_{50}$ at 2 hr was expected to be 80 nM and the IC$_{50}$ at 4 hr was expected to be 20 nM. However, the measured IC$_{50}$ at 2 hr was about 120 nM, which was much higher than the expected value of 80 nM. In addition, the measured IC$_{50}$ at 4 hr was about 80 nM, which was much higher than the expected value of 20 nM. Therefore, it was confirmed that the efficiency of aza-T-dCyd starting material (SM) greatly decreases as the exposure time of the compound to the cells increases. This suggests that exposing a higher amount of aza-T-dCyd starting material (SM) during a short period of time would provide an efficient treatment.

Therefore, the above data suggests that crystalline polymorphs having a great dissolution profile such as Form A or Form F in the present disclosure have benefits over aza-T-dCyd starting material (SM) and other crystalline polymorphs having an inferior dissolution profile. In addition, for the same reason, the above data suggests that crystalline polymorphs such as Form A or Form F of the present disclosure shows improved PK profiles than aza-T-dCyd starting material (SM) or other crystalline polymorphs.

Figure 20:
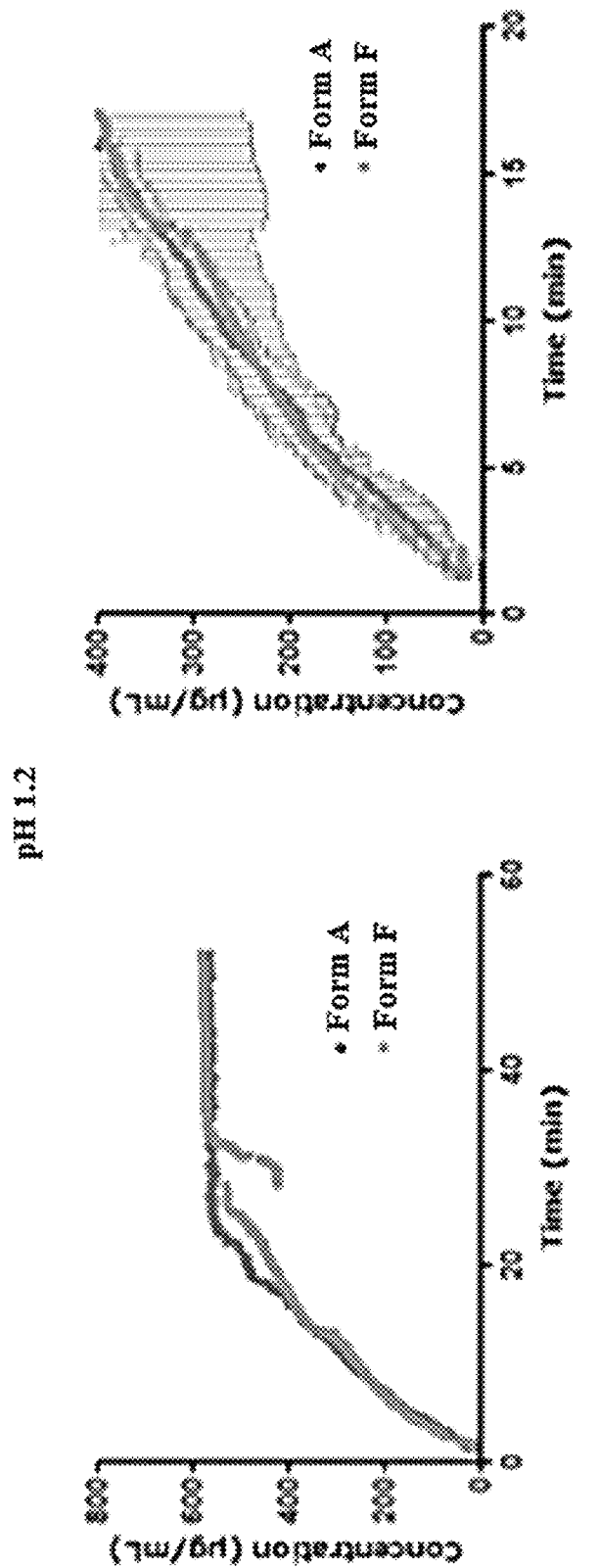
FIG. 20 shows dissolution rate profiles of Form A and Form B at pH 1.2.
Figure 21:
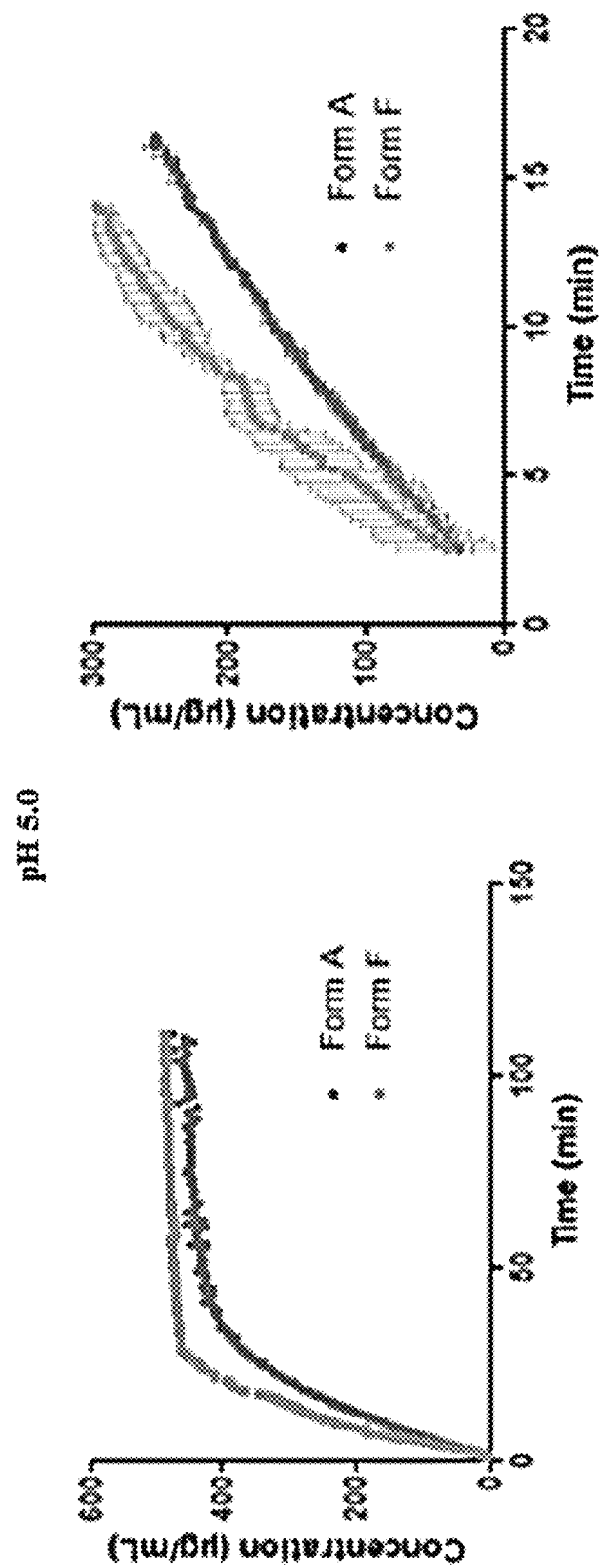
FIG. 21 shows dissolution rate profiles of Form A and Form B at pH 5.0.
Figure 22:
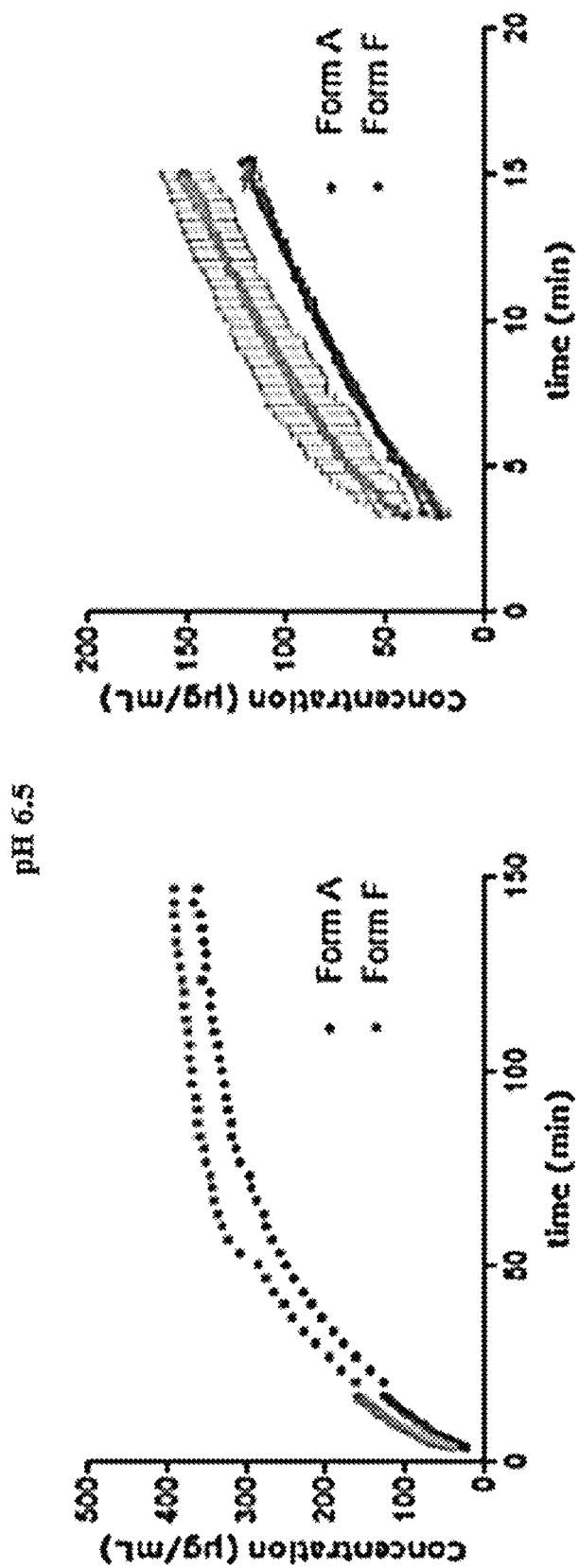
FIG. 22 shows dissolution rate profiles of Form A and Form B at pH 6.5.

9. Example 7: Dissolution Rate Profile of Form A and Form F at Various pH Points The dissolution rates of Form A and Form F at pH 1.2, pH 6.5 and pH 5.0 were measured, and presented in Table 6 and FIG. 20-22.

TABLE 6

| Form | Medium | pH | Linear range (min) | IDR (mg/mL/Cm$^2$/min) |
|---|---|---|---|---|
| A | SGF | 1.2 | 1-15 | 7.4 ± 0.21 |
|   | FaSSIF | 6.5 | 3-15 | 2.2 ± 0.06 |

TABLE 6-continued

| Form | Medium | pH | Linear range (min) | IDR (mg/mL/Cm²/min) |
|---|---|---|---|---|
|  | FeSSIF | 5.0 | 1-16 | 4.6 ± 0.07 |
| F | SGF | 1.2 | 2-10 | 7.0 ± 1.26 |
|  | FaSSIF | 6.5 | 3-15 | 2.7 ± 0.05 |
|  | FeSSIF | 5.0 | 2-16 | 6.0 ± 0.70 |

SGF: Simulated Gastrointestinal Fluid
FaSSIF: Fasted State Simulated Intestinal Fluid
FeSSIF: Fed State Simulated Intestinal Fluid As shown in Table 6 and FIG. 20-22, at pH 1.2 (pH condition of the stomach and large intestine), similar dissolution rates were shown in Form A and Form F while Form A showed a more consistent dissolution rate profile as compared to Form F. At pH 6.5 and pH 5 (pH condition of the appendix and small intestine), Form F showed a higher dissolution rate than Form A.

The above suggests that Form A may be prepared in various drug forms, which target to release an active ingredient of the drug at about pH 1.2 (e.g., the stomach or the large intestine). In addition, the above suggests that Form F may be prepared in various drug forms which target to release an active ingredient of the drug at about pH 5.0 to 6.5 (e.g., the small intestine).

10. Example 8: Pharmacokinetic Comparison of Aza-T-dCyd Starting Material, Form A and Form F The pharmacokinetic characteristics of aza-T-dCyd (starting material; SM; aza-T-dCyd that has not yet been subjected to specific crystallization conditions), Form A and From F were studied as follows.

Each of aza-T-dCyd starting material (SM), Form A, and Form F was prepared in the form of a capsule where each was mixed with microcrystalline cellulose at 8:92 (w/w), and can be administered to a rat at 2 mg/kg of SM, Form A, or Form F. Each of SM capsule, Form A capsule and Form F capsule was administered at 2 mg/kg dose to two male SD rats (i.e., six male SD rats in total). The plasma concentration of each SM, Form A, and Form F in the tested SD rats was measured at 0.25, 0.5, 1, 2, 4, 6, 8 and 24 hours after the administration of the capsule as shown in Tables 7-9.

TABLE 7

| | SM | | | | |
|---|---|---|---|---|---|
| Time | Concentration (ng/mL) | | Mean | SD | CV |
| (h) | Rat 5 | Rat 6 | (ng/mL) | (ng/mL) | (%) |
| 0.25 | 29.1 | 64.9 | 47.0 | 25.3 | 53.9 |
| 0.5 | 123 | 243 | 183 | 85 | 46.4 |
| 1 | 321 | 610 | 466 | 204 | 43.9 |
| 2 | 700 | 613 | 657 | 62 | 9.4 |
| 4 | 387 | 442 | 415 | 39 | 9.4 |
| 6 | 261 | 283 | 272 | 16 | 5.7 |
| 8 | 156 | 199 | 178 | 30 | 17.1 |
| 24 | 2.65 | 4.48 | 3.57 | 1.29 | 36.3 |

TABLE 8

| | FORM A | | | | |
|---|---|---|---|---|---|
| Time | Concentration (ng/mL) | | Mean | SD | CV |
| (h) | Rat 1 | Rat 2 | (ng/mL) | (ng/mL) | (%) |
| 0.25 | 77.2 | 511 | 294 | 307 | 104.3 |
| 0.5 | 254 | 721 | 488 | 330 | 67.7 |
| 1 | 815 | 912 | 864 | 69 | 7.9 |
| 2 | 677 | 645 | 661 | 23 | 3.4 |
| 4 | 556 | 420 | 488 | 96 | 19.7 |
| 6 | 397 | 307 | 352 | 64 | 18.1 |
| 8 | 261 | 210 | 236 | 36 | 15.3 |
| 24 | 6.71 | 4.29 | 5.50 | 1.71 | 31.1 |

TABLE 9

| | FORM F | | | | |
|---|---|---|---|---|---|
| Time | Concentration (ng/mL) | | Mean | SD | CV |
| (h) | Rat 3 | Rat 4 | (ng/mL) | (ng/mL) | (%) |
| 0.25 | 225 | 394 | 310 | 120 | 38.6 |
| 0.5 | 755 | 780 | 768 | 18 | 2.3 |
| 1 | 886 | 982 | 934 | 68 | 7.3 |
| 2 | 746 | 764 | 755 | 13 | 1.69 |
| 4 | 536 | 377 | 457 | 112 | 24.6 |
| 6 | 362 | 285 | 324 | 54 | 16.8 |
| 8 | 245 | 199 | 222 | 33 | 14.7 |
| 24 | 7.04 | 3.81 | 5.43 | 2.28 | 42.1 |

In addition, the pharmacokinetic parameters were obtained as shown in Tables 10-12 below.

TABLE 10

| | SM | | | | | |
|---|---|---|---|---|---|---|
| PK parameters | Unit | Rat 5 | Rat 6 | Mean | SD | CV(%) |
| $T_{1/2}$ | h | 2.72 | 2.98 | 2.85 | 0.18 | 6.37 |
| $T_{max}$ | h | 2.00 | 2.00 | 2.00 | 0.00 | 0.000 |
| $C_{max}$ | ng/mL | 700 | 613 | 657 | 62 | 9.4 |
| $AUC_{last}$ | h*ng/mL | 4065 | 4761 | 4413 | 492 | 11.1 |
| $AUC_{Inf}$ | h*ng/mL | 4076 | 4780 | 4428 | 498 | 11.3 |
| $AUC\_{\%Extrap}\_obs$ | % | 0.255 | 0.402 | 0.329 | 0.104 | 31.7 |
| $MRT_{Inf}\_obs$ | h | 5.06 | 5.23 | 5.15 | 0.12 | 2.36 |
| $AUC_{last}/D$ | h*mg/mL | 2033 | 2381 | 2207 | 246 | 11.1 |
| F | % | NA | NA | NA | NA | NA |

TABLE 11

FORM A

| PK parameters | Unit | Rat 1 | Rat 2 | Mean | SD | CV(%) |
|---|---|---|---|---|---|---|
| $T_{1/2}$ | h | 3.05 | 2.89 | 2.97 | 0.11 | 3.64 |
| $T_{max}$ | h | 1.00 | 1.00 | 1.00 | 0.00 | 0.0 |
| $C_{max}$ | ng/mL | 815 | 912 | 864 | 69 | 7.9 |
| $AUC_{last}$ | h*ng/mL | 6050 | 5428 | 5739 | 440 | 7.7 |
| $AUC_{Inf}$ | h*ng/mL | 6079 | 5446 | 5763 | 448 | 7.8 |
| $AUC_{\%Extrap}\_obs$ | % | 0.485 | 0.329 | 0.407 | 0.110 | 27.1 |
| $MRT_{Inf}\_obs$ | h | 5.40 | 4.83 | 5.11 | 0.41 | 7.94 |
| $AUC_{last}/D$ | h*mg/mL | 3025 | 2714 | 2869 | 220 | 7.7 |
| F | % | NA | NA | NA | NA | NA |

TABLE 12

FORM F

| PK parameters | Unit | Rat 3 | Rat 4 | Mean | SD | CV(%) |
|---|---|---|---|---|---|---|
| $T_{1/2}$ | h | 3.15 | 2.86 | 3.00 | 0.21 | 6.90 |
| $T_{max}$ | h | 1.00 | 1.00 | 1.00 | 0.00 | 0.000 |
| $C_{max}$ | ng/mL | 886 | 982 | 934 | 68 | 7.3 |
| $AUC_{last}$ | h*ng/mL | 6180 | 5419 | 5800 | 538 | 9.28 |
| $AUC_{Inf}$ | h*ng/mL | 6212 | 5435 | 5823 | 550 | 9.44 |
| $AUC_{\%Extrap}\_obs$ | % | 0.515 | 0.289 | 0.402 | 0.160 | 39.8 |
| $MRT_{Inf}\_obs$ | h | 5.09 | 4.63 | 4.86 | 0.33 | 6.71 |
| $AUC_{last}/D$ | h*mg/mL | 3090 | 2709 | 2900 | 269 | 9.28 |
| F | % | NA | NA | NA | NA | NA |

As shown above, both of Form A and Form F showed grater $C_{max}$ values as compared to SM. In particular, Form A showed about 1.3 times higher Cmax value than SM, and Form F showed about 1.4 times higher Cmax value than SM. In addition, both of Form A and Form F showed AUC values which are about 30% higher than SM.

11. Example 9: Half Maximal Inhibitory Concentration ($IC_{50}$) Comparison of Aza-T-dCyd Starting Material and Form A K562 and HL-60 cell lines were cultured and maintained in RPMI (10% FBS, 1% Penicillin-Streptomycin) medium at 37° C., 95% Air, and 5% $CO_2$. K562 and HL-60 cell lines were each seeded in 96-well plates at a density of 3000 cells/well (90 μl). Form A and SM were treated in each well at a final concentration of 10 μM by treating 10 μl using 3-fold dilution. The cells were incubated for 3 days at 37° C., 95% Air, and 5% $CO_2$. 96-well plates were placed in room temperature for 30 minutes in order to equilibrate. Then, 100 μl of CellTiter-Glo® Luminescent Cell Viability Assay Reagent was added in 96-wells and incubated for 10 minutes in room temperature. Luminescence was measured using Luminometer and $IC_{50}$ value was analyzed using Graph-Prism.

Figure 23:
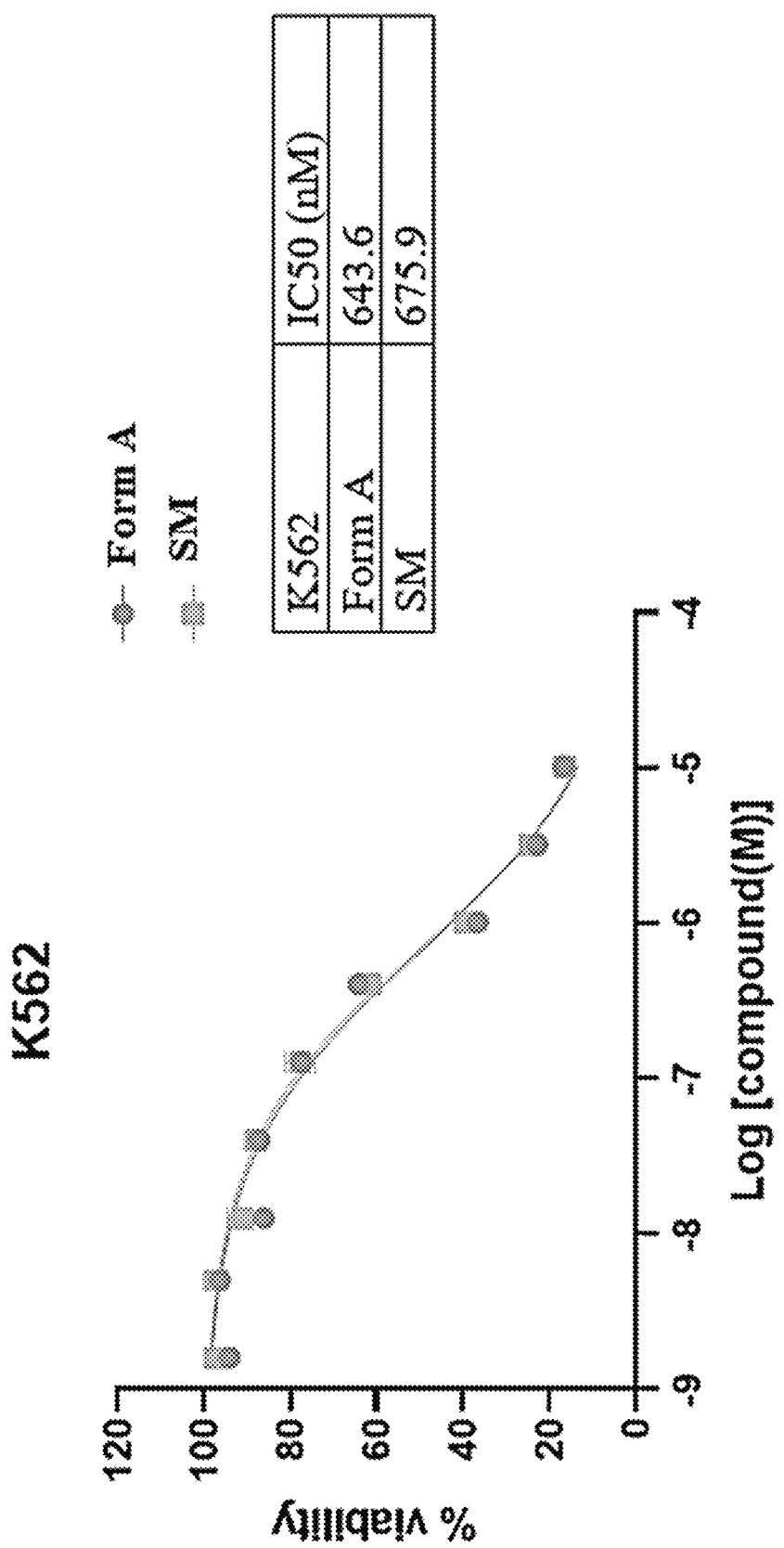
FIG. 23 shows $IC_{50}$ values when K562 cell lines were treated with Form A or SM.
Figure 24:
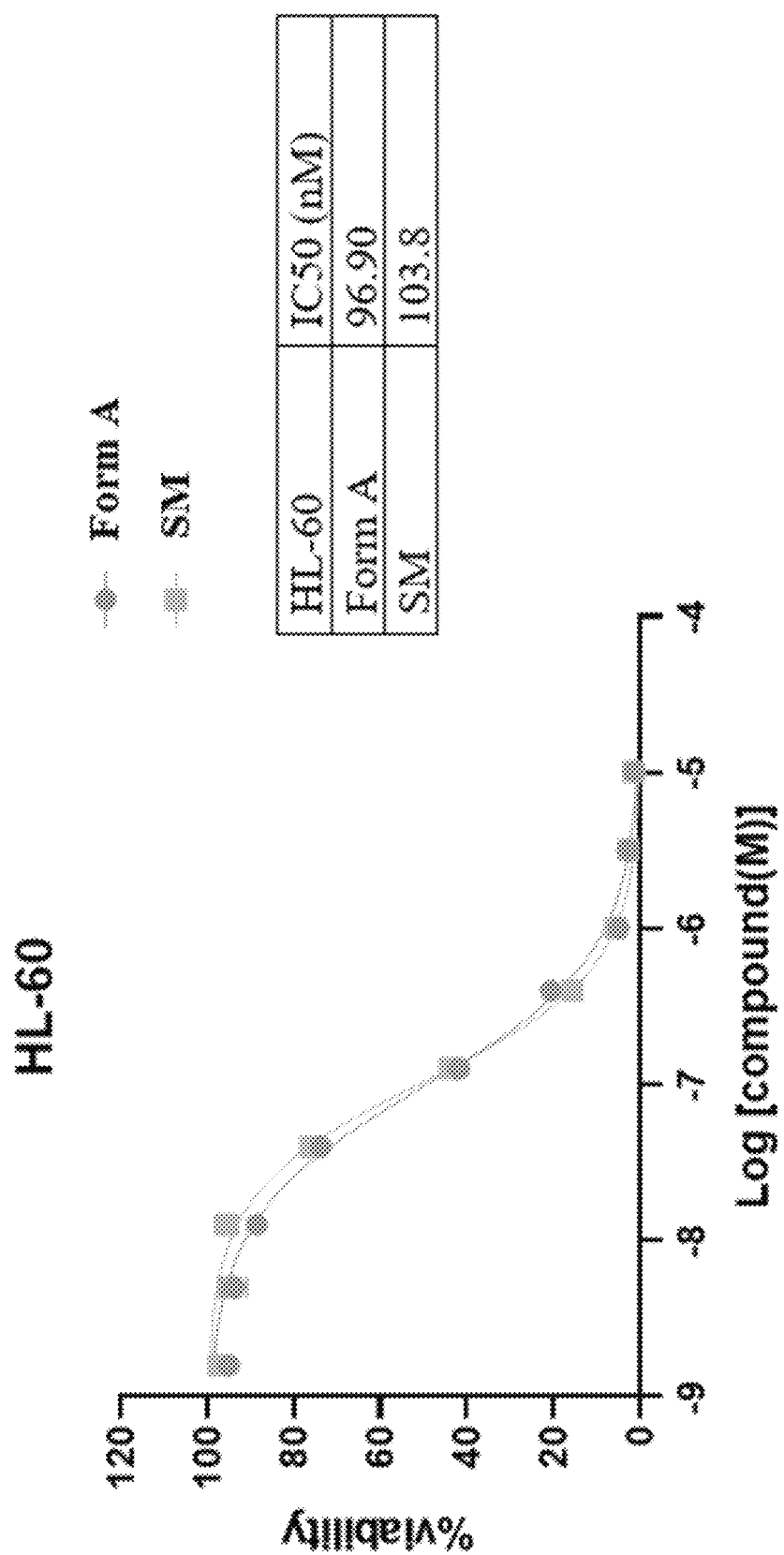
FIG. 24 shows $IC_{50}$ values when HL-60 cell lines were treated with Form A or SM.

As shown in FIG. 23 and FIG. 24, Form A showed about 5% lower $IC_{50}$ value than SM, and thus provides greater effects.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A crystalline polymorph of 5-aza-4'-thio-2'-deoxycytidine, wherein the crystalline polymorph has a powder X-ray diffraction pattern that contains peaks at about 8°, about 13°, about 15°, about 17°, about 19°, about 22°, about 23° about 26°, about 28°, about 29°, about 31°, about 33°, and about 37° 2θ.

2. The crystalline polymorph of claim 1, wherein the crystalline polymorph has an X-ray powder diffraction pattern that is substantially similar to, or the same as, the X-ray powder diffraction pattern shown in FIG. 11.

3. A pharmaceutical composition comprising an effective amount of the crystalline polymorph of claim 1 and a pharmaceutically acceptable carrier.

4. An 5-aza-4'-thio-2'-deoxycytidine compound consisting of the crystalline polymorph of claim 1.

5. A crystalline polymorph of 5-aza-4'-thio-2'-deoxycytidine, wherein the crystalline polymorph has a powder X-ray diffraction pattern that contains peaks at about 6°, about 12°, about 13°, about 14°, about 16°, about 18°, about 20°, about 21°, about 22°, about 26°, about 27°, about 29°, about 30°, about 33°, about 35°, about 36°, about 39°, and about 41° 2θ.

6. The crystalline polymorph of claim 5, which exhibits an X-ray powder diffraction pattern substantially similar to, or the same as, the X-ray powder diffraction pattern shown in FIG. 16.

7. A pharmaceutical composition comprising an effective amount of the crystalline polymorph of claim 5 and a pharmaceutically acceptable carrier.

8. An 5-aza-4'-thio-2'-deoxycytidine compound consisting of the crystalline polymorph of claim 5.

9. A method of treating a cancer in a subject in need thereof, the method comprising administering to the subject an effective amount of the crystalline polymorph of claim 1.

10. The method of claim 9, wherein the cancer is a blood cancer.

11. The method of claim 10, wherein the blood cancer is selected from the group consisting of non-Hodgkin's lymphoma, Hodgkin's lymphoma, multiple myeloma, leukemia, lymphoma, myelodysplastic syndrome, acute lymphocytic leukemia, acute myelogenous leukemia, chronic lymphocytic leukemia, chronic myeloid leukemia, and solitary myeloma.

12. The method of claim 9, wherein the cancer is a solid cancer.

13. The method of claim 9, wherein administering is via a treatment cycle.

14. The method of claim 13, wherein each treatment cycle includes administering the effective amount of the compound for a time period of from about 4 days to about 6 days.

15. The method of claim 9, wherein the administering is via a course of treatment comprising:
   a first treatment cycle that includes administering the effective amount of the crystalline polymorph for a time period of from about 4 days to about 6 days;
   a first rest period that includes abstaining from administering the crystalline polymorph for a time period of about 1 day to about 3 days;
   a second treatment cycle that includes administering the effective amount of the crystalline polymorph for a time period of from about 4 days to about 6 days; and
   a second rest period that includes abstaining from administering the crystalline polymorph for a time period of at least about 8 days.

16. A method of treating a cancer in a subject in need thereof, the method comprising administering to the subject an effective amount of the crystalline polymorph of claim 5.

17. The method of claim 16, wherein the cancer is a blood cancer.

18. The method of claim 17, wherein the blood cancer is selected from the group consisting of non-Hodgkin's lymphoma, Hodgkin's lymphoma, multiple myeloma, leukemia, lymphoma, myelodysplastic syndrome, acute lymphocytic leukemia, acute myelogenous leukemia, chronic lymphocytic leukemia, chronic myeloid leukemia, and solitary myeloma.

19. The method of claim 16, wherein the cancer is a solid cancer.

20. The method of claim 16, wherein administering is via a treatment cycle.

21. The method of claim 20, wherein each treatment cycle includes administering the effective amount of the compound for a time period of from about 4 days to about 6 days.

22. The method of claim 16, wherein the administering is via a course of treatment comprising:
   a first treatment cycle that includes administering the effective amount of the crystalline polymorph for a time period of from about 4 days to about 6 days;
   a first rest period that includes abstaining from administering the crystalline polymorph for a time period of about 1 day to about 3 days;
   a second treatment cycle that includes administering the effective amount of the crystalline polymorph for a time period of from about 4 days to about 6 days; and
   a second rest period that includes abstaining from administering the crystalline polymorph for a time period of at least about 8 days.

* * * * *